(12) United States Patent
Paraschiv et al.

(10) Patent No.: US 12,119,106 B1
(45) Date of Patent: Oct. 15, 2024

(54) SYSTEM AND METHOD FOR FACILITATING MULTI-PROVIDER PATIENT DISCHARGE WITH THE AID OF A DIGITAL COMPUTER

(71) Applicant: Health Care Solutions Inc., Woodinville, WA (US)

(72) Inventors: Iulian Vladimirovich Paraschiv, Boise, ID (US); Michael Anatolyevich Nikitin, Kirkland, WA (US); Oleksii Chyzhmakov, Kyiv (UA)

(73) Assignee: Health Care Solutions Inc., Woodinville, WA (US)

( * ) Notice: Subject to any disclaimer, the term of this patent is extended or adjusted under 35 U.S.C. 154(b) by 699 days.

(21) Appl. No.: 17/360,306

(22) Filed: Jun. 28, 2021

Related U.S. Application Data

(63) Continuation-in-part of application No. 15/969,645, filed on May 2, 2018, now Pat. No. 11,049,607.
(Continued)

(51) Int. Cl.
| | |
|---|---|
| *G16H 40/20* | (2018.01) |
| *G06F 21/60* | (2013.01) |
| *G16H 10/60* | (2018.01) |
| *G16H 50/70* | (2018.01) |
| *H04L 9/40* | (2022.01) |

(52) U.S. Cl.
CPC .......... *G16H 40/20* (2018.01); *G06F 21/602* (2013.01); *G16H 10/60* (2018.01); *G16H 50/70* (2018.01); *H04L 63/0428* (2013.01)

(58) Field of Classification Search
CPC .............................. G16H 40/20; G16H 10/60
See application file for complete search history.

(56) References Cited

U.S. PATENT DOCUMENTS

| 8,065,167 B1 | 11/2011 | Wyman |
|---|---|---|
| 9,832,069 B1 | 11/2017 | Cleveland et al. |
| (Continued) | | |

FOREIGN PATENT DOCUMENTS

| WO | 2018005828 | 1/2018 |
|---|---|---|

OTHER PUBLICATIONS

What to Look for When Touring a Nursing Home, 2016, Next Avenue (Year: 2016).
(Continued)

*Primary Examiner* — Karen A Hranek
(74) *Attorney, Agent, or Firm* — Leonid Kisselev

(57) ABSTRACT

Data from a plurality of parties involved in a discharge of the patient is securely processed in a cloud-computing environment. The cloud-computing environment identifies service providers suitable for the patient using a plurality of matching criteria and information derived at least in part from discharge information provided by the facility from which the patient is being discharged, and can contact the service providers to determine whether the service providers are willing to start caring for the patient. The decision to discharge the patient to a care of a particular suitable care provider and the decision by the care provider to accept such patient to the provider's care can be also be automated. The cloud-computing environment can further update the discharge information based on a request from the service providers. The cloud-computing environment securely stores the data received from all parties.

17 Claims, 13 Drawing Sheets

Related U.S. Application Data

(60) Provisional application No. 62/500,392, filed on May 2, 2017.

(56) References Cited

U.S. PATENT DOCUMENTS

| | | |
|---|---|---|
| 2008/0312972 A2 | 12/2008 | Rosow et al. |
| 2013/0339040 A1 | 12/2013 | Bracken et al. |
| 2014/0100876 A1 | 4/2014 | Savage et al. |
| 2014/0316812 A1 | 10/2014 | Hathorn et al. |
| 2015/0213571 A1 | 7/2015 | Chambers et al. |
| 2015/0254405 A1* | 9/2015 | Phillips .................. G16H 10/60 705/2 |
| 2015/0310184 A1 | 10/2015 | Yui et al. |
| 2016/0070712 A1 | 3/2016 | Prabhakar et al. |
| 2016/0132650 A1 | 5/2016 | Kejriwal et al. |
| 2016/0371439 A1 | 12/2016 | Salazar et al. |
| 2017/0084070 A1* | 3/2017 | Chamdani .............. G16H 50/30 |
| 2018/0276341 A1 | 9/2018 | Rab et al. |
| 2018/0308150 A1* | 10/2018 | Tolvanen ............ G06F 16/9537 |
| 2019/0096523 A1* | 3/2019 | Taniguchi ............... G16H 40/20 |
| 2021/0134445 A1* | 5/2021 | Pandya .................. G16H 80/00 |

OTHER PUBLICATIONS https://fhir.epic.com/Documentation?docId=oauth2&section=EmbeddedOauth2Launch (Printed on Jul. 7, 2021).

* cited by examiner

| ENABLED | PRIORITY | SHOW BY DEFAULT | TITLE | NOTE TYPES | UPDATE SCHEDULE | |
|---|---|---|---|---|---|---|
| ON | 1 | ON | Face Sheet | | Start: 2021-06-01 00:00 Interval: 10 Hours | |
| ON | 2 | ON | Medication Administration Record | | Start: Date and Time Interval: 0 Days | |
| ON | 3 | ON | Active Lab & Imaging Orders | | Start: Date and Time Interval: 0 Days | |
| ON | 4 | ON | Completed Lab & Imaging Orders | | Start: Date and Time Interval: 0 Days | |
| ON | 5 | ON | Laboratory Results | | Start: Date and Time Interval: 0 Days | |
| ON | 7 | ON | Progress Notes | 1 | Start: Date and Time Interval: 0 Days | Delete |
| NO | 8 | ON | Care Plan Notes | 200004 | Start: Date and Time Interval: 0 Days | Delete |
| ON | 9 | NO | History & Physical | 4,100001 | Start: Date and Time Interval: 0 Days | Delete |
| NO | 10 | ON | Nursing Notes | 200000 | Start: Date and Time Interval: 0 Days | Delete |
| ON | 11 | ON | Consult Notes | 2 | Start: Date and Time Interval: 0 Days | Delete |
| ON | 12 | NO | Procedure Notes | 3 | Start: Date and Time Interval: 0 Days | Delete |
| ON | 13 | ON | ED Notes | 6,8,19 | Start: Date and Time Interval: 0 Days | Delete |
| NO | 14 | ON | Ancillary Notes | 200002 | Start: Date and Time Interval: 0 Days | Delete |
| ON | 15 | ON | Wound Care Notes | 100111 | Start: Date and Time Interval: 0 Days | Delete |
| ON | 16 | ON | Discharge Summary | 5 | Start: Date and Time Interval: 0 Days | Delete |
| ON | 16 | NO | Notes Summary | 1,2,3,5,6,7,8,9,10,11,12,13,14,19,20 | Start: Date and Time Interval: 0 Days | Delete |
| ON | 6 | NO | Lines, Drains, Airways, Wounds | | Start: Date and Time Interval: 0 Days | |
| ON | 6 | NO | Vital Signs | | Start: Date and Time Interval: 0 Days | |
| ON | 6 | NO | Outpatient Medication List | | Start: Date and Time Interval: 0 Days | |
| ON | 6 | NO | Immunizations | | Start: Date and Time Interval: 0 Days | |
| ON | 6 | NO | Allergies | | Start: Date and Time Interval: 0 Days | |
| NO | 7 | NO | Last Bowel Movement | | Start: Date and Time Interval: 0 Days | |
| NO | | NO | | | | +Add |

| ENABLED | CALL # | NOTE TYPES | USE CONTACT ID | STATUSES | LOOK BACK DAYS FROM ADMIT | ACTIONS |
|---|---|---|---|---|---|---|
| ON | 1 | 4,10001 | ON | 2,3 | 30 | Delete |
| ON | 2 | 2,3 | ON | 2,3 | 2 | Delete |
| NO | 3 | 1,5,6,8,19,200000 | ON | 2,3 | 3 | Delete |
| ON | 4 | 200002,100111,200004 | ON | 2,3 | 14 | Delete |
| | 5 | 1,5,6,8,19 | ON | 2,3 | 3 | Delete |
| ON | 6 | 1,5 | ON | 2,3 | Admit_date | Delete |
| ON | 7 | 1,2,3,5,7,8,9,10,11,12,13,14,19,20 | NO | 2,3 | Admit_date | Delete |
| NO | | | NO | | | +Add |

SYSTEM AND METHOD FOR FACILITATING MULTI-PROVIDER PATIENT DISCHARGE WITH THE AID OF A DIGITAL COMPUTER

CROSS-REFERENCE TO RELATED APPLICATION

This non-provisional patent application is a continuation-in-part of U.S. Pat. No. 11,049,607, issued Jun. 29, 2021, which claims priority under 35 U.S.C. § 119(e) to U.S. Provisional Patent application Ser. No. 62/500,392, filed May 2, 2017, the disclosures of which are incorporated by reference.

FIELD

This invention relates in general to electronic communications, and in particular, to a system and method for facilitating multi-provider patient discharge with the aid of a digital computer.

BACKGROUND

While healthcare facilities such as hospitals offer the highest quality of a patient care, a patient generally does not stay in such a facility for an extended period of time, and eventually must be discharged. Depending on the condition of the patient, the patient may not be discharged to his or her home, and instead require acceptance to a long-term care facility ("LTCF"), such as a nursing home, a licensed residential care home (adult family/foster home), a skilled nursing facility, or an assisted living facility. Further, rarely does a discharged patient require care of only a single kind of entity. Thus, a patient discharged to an LTCF may also need to be serviced by a pharmacy, a provider of medical devices (such as a provider of prosthetics or walking aids or cardiac pacing or monitoring devices), or various therapists, or other kinds of medical services, such as dialysis.

Currently, once the discharge date of a patient is known, the patient or a representative of the patient, such as a relative or a placement agent in a hospital, must engage in a manual search of a suitable LTCF. Generally, the patient and the patient's representative are given a stack of brochures and verbal instructions about different options. However, the patient and any representative are often under a high level of stress and neither retain a significant amount of the given instructions nor find such brochures useful. Further, as the number of types of different service providers to whose care the patient needs to be discharged grows, the amount of information with which the patient and patient's representatives are presented also grows.

As a result, left without a better option, the patient or the patient's representative is forced to call over the phone a large number of LTCFs and other types of service providers in the patient's geographic area to learn availability and types of care provided in those facilities. If an LTCF has availability and provides care close to what the patient needs, the patient or the representative may visit facility in person for a tour. Such placement efforts typically takes weeks, sometimes extending to months, and such efforts may not even start until a qualified medical professional conducts an assessment of the patient necessary for the discharge. Finding suitable service providers of other types presents even further delays. During this time, the patient generally resides in the original facility, experiencing a now-mismatched level of care, as well as confusion, stress, and possible cycles of hospital discharges and readmissions. Residing at the original facility, such as an acute care hospital, is further associated with higher costs to the hospital or to the patient than the patient would be burdened with at a suitable LTCF and suitable service providers of other types.

Patient discharge is further complicated due to a lack of communication between different facilities involved in the discharge, such as a hospital and an LTCF and service providers of other types. Due to a high level of patient privacy requirements imposed by Health Insurance Portability and Accountability Act (HIPAA) as well as other similar legislations, the facilities may be unable to directly share patient data with another organization. As a result, the patient representative may be forced to physically carry the necessary documentation from one facility to another.

Accordingly, there is a need for a secure system that allows to identify a suitable service providers of multiple types for a patient's discharge. There is a further need for a way to provide critical information in real time about service provider availability and type of care such care providers can provide. There is a still further need for caregivers and sometimes the patients themselves to be able to access a system where important information can be securely sent to and received from service providers.

SUMMARY

The technical and administrative difficulties as well as the long-delays associated with a conventional discharge to care of providers of multiple types, including a long-term care facility, are remedied through a system and method described below. Data from a plurality of parties involved in a discharge of the patient is securely processed in a cloud-computing environment. The cloud-computing environment identifies service providers suitable for the patient using a plurality of matching criteria and information derived at least in part from discharge information provided by the facility from which the patient is being discharged, and can contact the service providers to determine whether the service providers are willing to start caring for the patient. The decision to discharge the patient to a care of a particular suitable care provider and the decision by the care provider to accept such patient to the provider's care can be also be automated, with the cloud-computing environment auto-discharging the patient from the discharging facility and auto-accepting the patient into an automated based on pre-determined criteria. The cloud-computing environment can further update the discharge information based on a request from the service providers, allowing them to make the acceptance decision based on the up-to-date information about the patient. The cloud-computing environment securely stores the data received from all parties, protecting patient information in accordance with relevant laws, and can provide access to such information to authorized parties in near-real-time. The cloud-computing environment also verifies relevant licensing status of parties involved in the discharge to further preserve patient safety, and schedule necessary activities by such parties, such as finding an individual capable of performing an assessment of the patient.

In one embodiment, a system and method for cloud-based facilitation of multi-provider patient discharge with the aid of a digital computer are provided. Obtained by one or more of a plurality of background process servers included within a cloud-computing environment is information regarding a plurality of service providers of different types located in multiple jurisdictions, the service provider information including a geographic location of each of the service providers within one of the multiple jurisdictions and care capabilities of the service providers. Received, via one of a plurality of Internetworks, by a load balancing service included within the cloud-computing environment and implemented by one or more servers, from a computing device associated with one of a plurality of discharging facilities, each discharging facility located in one of the multiple jurisdictions, is encrypted discharge information for one of a plurality of patients, each patient located in one of the multiple jurisdictions, the discharge information including care needs of the patient, medical information of the patient, and geographic preferences of the patient for being discharged to a care of the service providers of at least two of the types. Provided, by the load balancing service, is the received discharge information to one of a plurality of web servers included within the cloud computing environment, and assigned by the load balancing service is performance of encrypted communication with that computing device to that web server, wherein the web servers and the background process servers communicate via a message queuing service included within the cloud computing environment, and wherein the web server stores session data regarding the encrypted communication within the cloud-computing environment. Compared by the web serve is, the service provider information to the discharge information for the patient. Identifying, by the web server, are one or more of the service providers of each of the at least two types suitable for the patient based on the comparison. Identifying, by the web server, at least one suitable service provider of each of the at least two types willing to accept the patient into their care. The patient is caused at least in part to be discharged to the care of one of the ready service providers of each of the at least two types by one or more of the web servers. Received by one or more of the web servers from one of the computing devices associated with the ready service providers a confirmation that the patient has been discharged to the care of those service providers.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 12 is a diagram showing an intake questionnaire for service providers in accordance with one embodiment.

FIG. 13 is a diagram showing a user interface for setting configurations for updating discharge information by a service provider in accordance with one embodiment.

DETAILED DESCRIPTION

Figure 1:
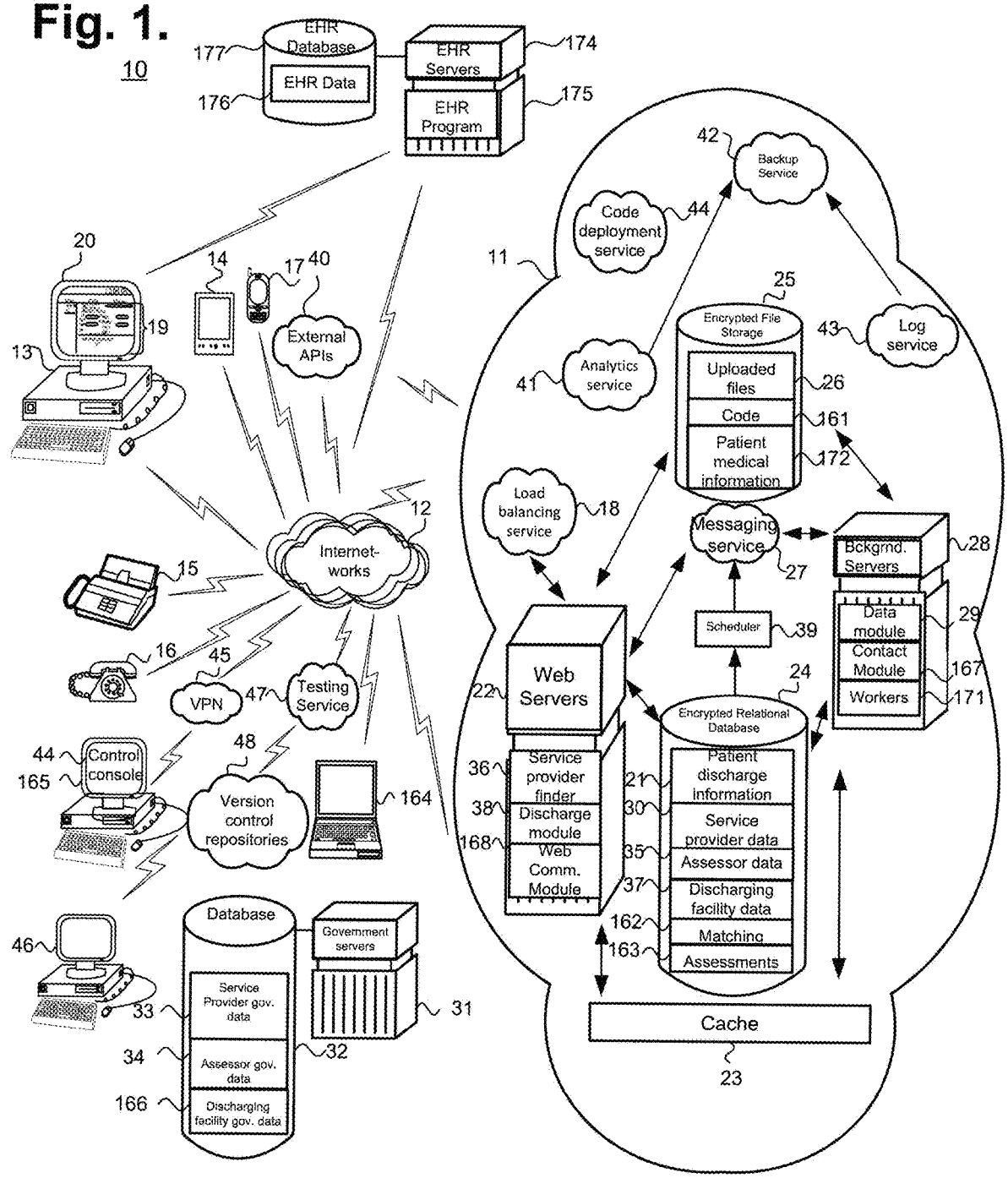
FIG. 1 is a block diagram showing a system for facilitating multi-provider patient discharge with the aid of a digital computer in accordance with one embodiment.

Patient discharge to the care of multiple service providers can be simplified and accelerated in a secure manner through a use of the system and method described below. FIG. 1 is a block diagram showing a system 10 for facilitating multi-provider patient discharge with the aid of a digital computer in accordance with one embodiment. The system includes a cloud-computing environment 11 that is interfaced to one or more Internetworks 12, such as the Internet, a cellular network, and a landline telephone network, though other kinds of Internetworks 12 are possible. Via one or more of the Internetworks 12, the cloud-computing environment 11 can communicate with a multitude of computing devices 13-16 associated with parties involved in discharge of a patient and acceptance of the patient to a care of a service providers of multiple types. Such service providers can include long-term care facility (LTCF), such as a nursing home, a licensed residential care home (adult family/foster home), a skilled nursing facility, or an assisted living facility, though other kinds of LTCFs are also possible. Other types of service providers can include pharmacies, providers of medical devices (such as a provider of prosthetics or walking aids or cardiac pacing or monitoring devices), or various therapists whose services are not regularly available at an LTCF. The service providers can provide still other kinds of medical services, such as dialysis. Still other types of service providers are possible.

Such computing devices can include a device 13 associated with the party discharging the patient, such as a hospital. While the computing device 13 is shown with reference to FIG. 1 to be a desktop computer, other kinds of computing devices 13, such as laptop computers, smartphones, and tablets, are possible. Similarly, while computing devices 14 and 164 are shown as a tablet and a laptop computer respectively, such devices can be other computing devices capable of connecting to one of the Internetworks.

Further, while in the description below a hospital is referred to as a discharging facility, in a further embodiment, an LTCF could be a discharging facility and a hospital could be a service provider to whose care the patient needs to be discharged as a condition of a patient at an LTCF may worsen to the extent that readmission to a hospital becomes necessary.

The computing device 13 associated with the discharging facility can start a cascade of events that can lead to a discharge of the patient and an acceptance of the patient to an LTCF and other types of a service provider. The discharging facility can further be associated with one or more Electronic Health Records (EHR) servers 174 that implement an EHR program 175 that manages EHR data 176 associated with the patients of the discharging facility and that is stored in an EHR database 177. The discharge information 21 (described below) originates as part of the EHR data 176. In one embodiment, the EHR program 175 can be implemented using the Fast Healthcare Interoperability Resources (FHIR) standard for format and other elements, and in particular, uses the FHIR API (which use HTTP-based RESTful protocols) for exchanging the EHR data 176 (such as the discharge information 21) with other entities (such as the cloud-computing environment 11). In one embodiment, the FHIR standard can be the HL7 FHIR standard, with the EHR program 175 being developed by Epic Systems Corporation of Verona, Wisconsin, though other kinds of FHIR and non-FHIR EHR programs are possible. In one embodiment, the computing device 13 can be interfaced to the EHR servers 174 (such as via a local network) and communicate with the cloud computing environment via the EHR servers 174. In a further embodiment, other ways for communication between the computing device 13 and the cloud-computing environment 11, in addition or as an alternative to communication via the EHR servers 174, are possible.

As further described below, the cloud-computing environment 11 provides a user interface 19 the discharging facility computing device 13 can access via a web-browser 20 or a mobile application. The user interface 19 allows the discharging facility to initiate providing to the cloud-computing environment 11 discharge information 21 for the patient via the EHR servers 174. The discharge information 21 can include an identifying information of the patient being discharged, such as the patient's name and birthdate; the patient's weight; the patient's projected discharge date; the name and contact information of the patient's representative; a current location of the patient; any temporal restrictions or preferences for an assessment to be performed on the patient; a desired geographic location of an LTCF and any types of service providers where the patient needs to be accepted and a distance of (or serviced by) an LTCF and other types of service providers from that location that is acceptable to the patient; the desired types of an service provider where the patient is to be accepted, as well as any subtypes (subspecialties) of the service providers such as whether the LTCF is an adult family home, an assisted living facility, or a skilled nursing facility; financial and insurance information of the patient that is relevant for the acceptance of the patient to a service provider, such as the daily rate that the patient is prepared to pay; an information about the patient's health, care needs, medications, and physical and mental abilities that are relevant to whether a service provider can accept the patient into their care. As part of the discharge information, a user associated with the discharging facility, such as a hospital placement agent, can upload through the user interface relevant files, such as the patient's medication lists. The discharge information 21 can also include permissions for sharing of the provided information: what parties can access particular information, such as uploaded files or contact information. Still other kinds of discharge information 21 is also possible.

In providing the discharge information 21 and other communications necessary for to facilitate the discharge of the patient, the EHR servers 174 directly communicate with only one component of the cloud-computing environment 11. In particular, the cloud-computing environment 11 includes a load balancing service 18, which receives communications from computing device 13 (via one of the EHR servers 174) transmitted via one or more of the Internetworks 12, such as the Internet, and sends responses to such communications. In one embodiment, the load balancing service 18 can be one of Elastic Load Balancing products, such as an Application Load Balancer, distributed by Amazon Web Services, Inc. of Seattle, Washington; other kinds of load balancing service 18 are also possible. Similarly, other computing devices that communicate with the cloud-computing environment via the Internet, such as the computing device 14 associated with assessors described below or computing devices associated with LTCF 164 can further similarly communicate with the load balancing service 18 via the Internet.

As the legal and technical requirements for processing discharge information 21 associated with a discharging facility at a particular jurisdiction, use of a load balancer 18 allows to assign processing communications regarding the patient at that discharging facility to a web server 22 most technically suited for handling that communication. Also, as the cloud-computing environment 11 can include as many web-servers 22 as necessary for a simultaneous discharge of thousands (if not millions) of patients across a multitude of jurisdictions. The load balancing service 18 forwards the received communications to one of a plurality of web servers 22 included in the cloud-computing environment 11, assigning that web-server 22 to process communications with the computing devices 13 (such as via the EHR servers 174), 14, 164. In particular, each of the web-servers 22 executes a web communication module 168, which receives the communications forwarded by the load balancing service 18 and sends response communications via the load balancing service 18 to the computing devices 13 (via the EHR servers 174), 14, 164 via the load balancing service 18. The web servers 22 can be virtual servers or dedicated servers. In one embodiment, the web servers 22 can be an Amazon® Elastic Cloud Compute web servers provided by Amazon Web Services, Inc. of Seattle, Washington, though other kinds of the web servers 22 are also possible. When a web communication module 168 of the web-servers 22 generates a response communication for the computing devices 13, 14, 164, the web communication module 168 of the web-servers 22 forwards the communication to the load balancing service 18, which in turn sends the response communication to the computing device 13 via one of the Internetworks 12. The communications between the load balancing service 18 and the computing devices 13, 14, 164 are encrypted to preserve the privacy of the exchanged patient data.

In communicating with the computing device 13, 14, 164 a web-server 22 uses a cache 23 to store data for quick retrieval, such as session data 24 associated with a current interaction with the computing device 13, 14, 164 as well as keys used in authentication of the user and encryption of the messages exchanged between the web-server 22 and the computing devices 13, 14, 164. The web-server 22 also stores data received from the computing devices 13, 14, 164 in persistent storage: in an encrypted relational database 24 and an encrypted file storage 25. In one embodiment, the relational database 24 can be a database that is a part of Amazon® Relational Database Service provided by Amazon Web Services, Inc. of Seattle, Washington, and implemented using MySQL 7.1, though other kinds of relational databases 24 are possible. To increase the security of storage of the discharge information 21, the information 21 is separated into two components, with the encrypted components being stored in encrypted storage 24, 25, thus providing a double of layer of an encryption—thus, even if one of the storages 24, 25 is compromised and the double layer of encryption is decrypted, the attacker would not come into possession of complete discharge information 21. Thus, the web communication module 168 of a web server 22 stores the component of the discharge information 21 provided by the computing device 13 that includes patient identifying information (such as name, date of birth, and social security) into the encrypted relational database 24; however, the information stored in the relational database 24 does include medical information regarding the patient, such as lab results or chart notes. Instead, files 172 with such medical information that are provided as part of the discharge information are stored as in the encrypted file storage 25 along with other uploaded files 26. In one embodiment, the file storage 25 can be Amazon® S3 storage provided by Amazon Web Services, Inc. of Seattle, Washington, though other kinds of file storage are also possible. As mentioned above, in addition to the database 24 and the file storage 25, any data stored within the relational database 24 and the file storage 25 is encrypted prior to being stored there to help ensure compliance with patient privacy requirements, and the use of the data requires decryption.

The web-servers 22 further communicate via a message queuing service 27 with one or more of a plurality of background process servers 28 included in the cloud-computing environment 11. In one embodiment, the message queuing service 27 can be Amazon® Simple Queue Service, though other kinds of messaging services are possible. The background process servers 28 can be virtual servers or dedicated servers. In one embodiment, the background process servers 28 can be servers that are part of Amazon Web Services® Elastic Beanstalk Worker Environments provided by Amazon Web Services, Inc. of Seattle, Washington, though other kinds of background process servers are possible.

As described above, the EHR servers 174 communicate with one of the web-servers 22 (via the load balancer service 18) to provide the discharge information 21 regarding the patient to the cloud-computing environment 11. The communication can be through a FHIR API (either internal to the cloud-computing environment 11 or included as part of the EHR servers 174). The EHR program 175 and the web-server interacting with the EHR program can perform an authentication protocol to confirm the identity of the EHR program 175 and the cloud-computing environment 11, such as described in OAuth 2.0 Tutorial, available at https://fhir.epic.com/Documentation?docId=oauth2&section=EmbeddedOauth2Launch, the disclosure of which is incorporated by reference. Once the authentication is complete, the EHR server 174 initially provides (via the FHIR API) patient identifying information (such as first and last name, date of birth, and social security number) as part of the discharge information 21 to the web-communication module 168 of one of the web servers 22 (via the load balancing service 18). The web communication module 168 checks whether the patient has already been registered with the cloud-computing environment 11 (such as the patient discharge information 21 being stored in the encrypted relational database 24) and if not, registers the patient by placing the received identifying information as part of the patient discharge information 21 within the encrypted relational database 24. If already registered, or after the registration is performed, the web communication module 168 obtains from the EHR program 175 remaining discharge information 21 (such as patient medical information files 172 and types of service providers that are needed) and stores the received information 21 in the encrypted relational database 24 and the encrypted file storage 25 as described above.

Prior to performing the search for suitable service providers for the patient for whom the discharge information 21 is received, the web server 22 must check that the patient is ready for discharge from the discharging facility. The check can be done automatically (such as by the service provider finder 36) if the discharging facility has enabled (such as during registration with the cloud-computing environment 11) an "auto-discharge" feature. To enable the auto-discharge feature, the discharging facility must provide to the cloud-computing environment 11 criteria that the patient must meet in order to qualify for auto-discharge (such as particular medical parameters of the patient), with such auto-discharge criteria being stored as part of the discharge facility data 37. If the discharge information 21 for the patient satisfies the auto-discharge criteria of the discharging facility, the service provider finder 36 can proceed to identify the suitable service providers to whose care the patient can be discharged. If the patient does not meet the auto-discharge criteria or if the auto-discharge feature is not enabled for the discharging facility, a confirmation that the patient is to be discharged is required from an authorized user of the cloud-computing environment (such as a social worker or a nurse associated with the discharging facility).

Further, as time may pass between when discharge information 21 is received and when a final decision is made to accept a patient into a care of one or more service providers or when that discharge is effected, the discharge information for the patient may need to be updated to make sure that acceptance into care of particular service providers is still proper. Such updates can be performed by one or more of the background servers 28 based on instructions from the relevant service providers. Such instructions can be stored as part of the service provider data 30 and can either include a command to update the discharge information 21 at a particular instance, or a schedule at which a particular service provider requires to update the discharge information 21 for a patient that may be discharged into the care of that service provide (such as every day, or at a particular time of day, or at a particular time interval). As the cloud-computing environment 11 may be dealing with thousands (if not millions) of patients and a multitude of updates may need to performed at around the same time, the updates that need to be performed are listed in a queue (which can be stored using the message queuing service 27, though other locations are possible) and are performed in accordance with their order in the queue (first-in-first-out (FIFO)). Each update is performed by a worker 171, which each worker being a script implemented by one of the background servers 22. Only one worker 171 performs the updating of the discharge information 21 for a single patient. Each worker 171 performs the update of discharge information of a single patient at a time, and once done with updating the information 21 for the patient, moves to updating the discharge information 21 for another patient whose turn came up at the end of the queue. The multiple workers 171 deployed on updating the discharge information 171 for multiple patients work in parallel—one worker 171 starts updating the discharge information 21 for one of the patients while another worker 171 is working on updating the discharge information 21 for another patient. The workers 171 performing the updates in parallel helps to reduce the amount of time necessary to keep the information 21 for all of the patients up-to-date. Further, due to the workers 171 being part of the cloud-computing environment 11, the number of workers 171 deployed for updating the discharge information can be easily scaled up as the number of patients whose information 21 needs to be updated increases, thus making the cloud-computing implementation essential.

As mentioned above, updating the discharge information 21 can be done based on a command received from a computing device 164 device associated with a service provider. The updating can be done based on a click of a single button presented through the user interface presented on the device 164. The user interface can present a progress bar reporting the progress of the update using WebSocket APIs, though other ways to present the information are possible. Providing such a progress bar provides additional controls to the service providers over their interactions with the system. The updating of the discharge information by the workers 171 can be done in accordance with configurations set up by the service providers, with the updates concerning only the information selected by the service providers. Such configuration can be performed through a user interface provided through the computing device 164, such as shown with reference to FIG. 13. FIG. 13 is a diagram showing a user interface for setting configurations for updating discharge information by a service provider in accordance with one embodiment.

Once a web server 22 receives and stores patient discharge information 21 and any associated files 26, a message to take action regarding the received discharge information 21 is passed from the web server 22 to one of the background process servers 28 via the message queuing service 27. Similarly, as further described below, the background process servers 28 can pass messages via the message queuing service to the web servers 22 to take action, such as contacting one of the computing devices 13, 14, and 164. Likewise, both the web servers 22 and the background process servers can receive messages from a scheduler 39 within the cloud-computing environment via the message queuing service 27 with messages to take action, such as contacting a government server 31 at predefined intervals as described below or update other data that the scheduler 39 can retrieve from the relational database 24. In one embodiment, the scheduler 39 can be a Cron scheduler, though other kinds of schedulers are also possible.

Each of the background process servers 28 implements several components that enable the cloud-computing environment 11 to facilitate a discharge of the patient in response to receipt of the patient discharge information 21. Thus, each of the background process servers 28 implements a data module 29, which obtains and updates data 30 about service providers and data about other relevant parties necessary for facilitating the discharge. Thus, periodically, one of the background process servers 28 can contact via one of the Internetworks 12 one or more servers 31 associated with a government agency, such as of a state Department of Social and Health Services (DSHS), which are in turn interfaced to at least one database 32 storing publicly-available government data. Such government data can include information 33 regarding service providers that require government licensing (such as LTCFs or pharmacies), such an identifier of a service provider, such as the name and postal address of a service provider; contact information of a service provider, such as a phone and a fax number; and a service provider government license number and whether the license is current; data regarding when the service provider was inspected (if applicable) and inspection results; and if an inspection identified any issues, data about any citations issued to the service provider; and an availability of licensed placement spots ("beds" hereinafter) in that LTCF. Other kinds of service provider government information 33 is possible.

The identification (such as spelling) of the service provider name in the government data may not always be identical with the identification of the same service provider in a different website or between different government data sources 33. Accordingly, to compile the most complete information regarding the same service provider, the background process servers 28 can compare the identification information of the one service provider in multiple sources of information; identify differences between the identification information based on the comparison; assigning weight to the identified differences; and identify a match between the identification information if the weighted differences are below a preset threshold.

Figure 2:
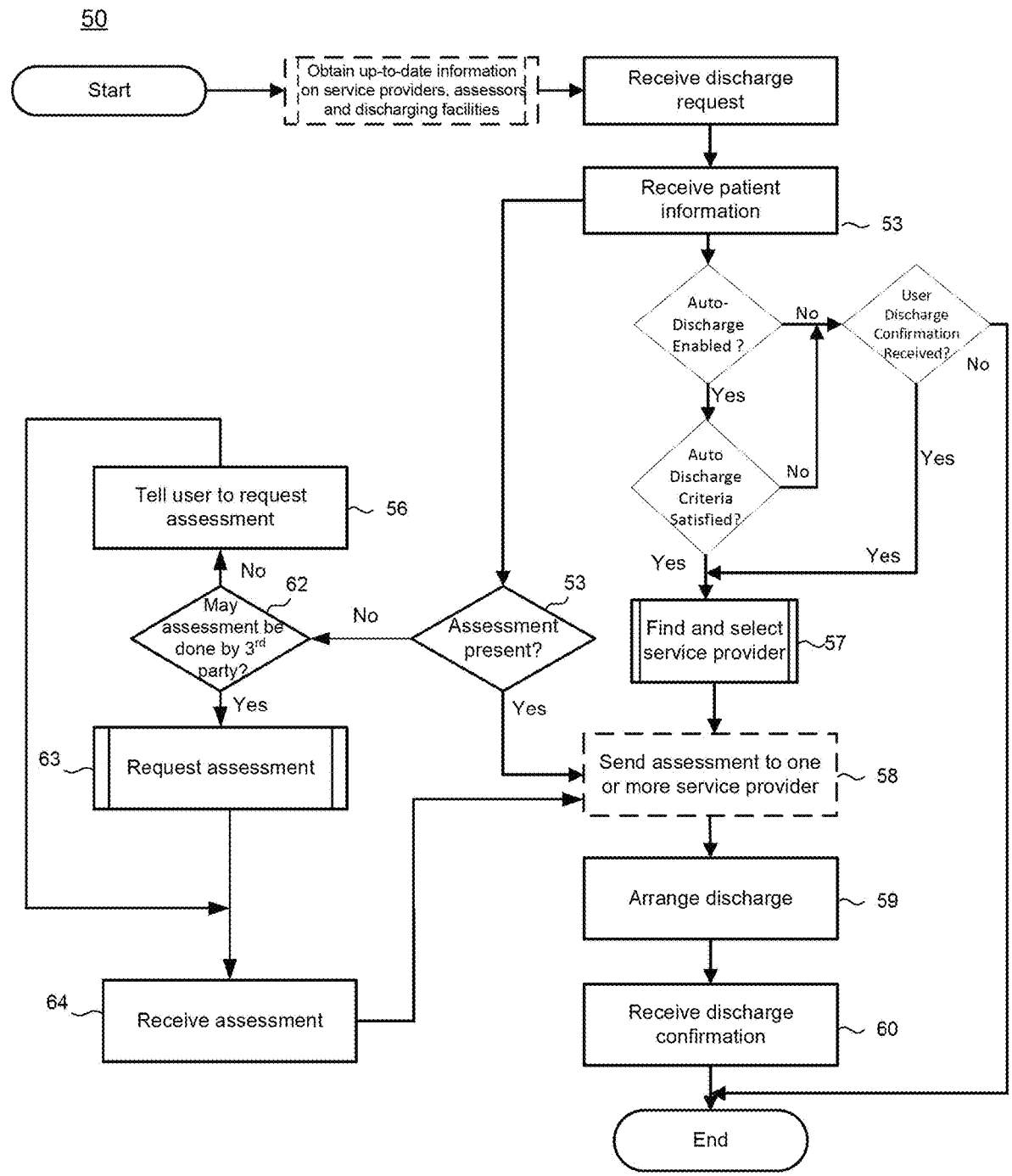
FIG. 2 is a flow diagram showing a method for facilitating multi-provider patient discharge with the aid of a digital computer in accordance with one embodiment.
Figure 12:
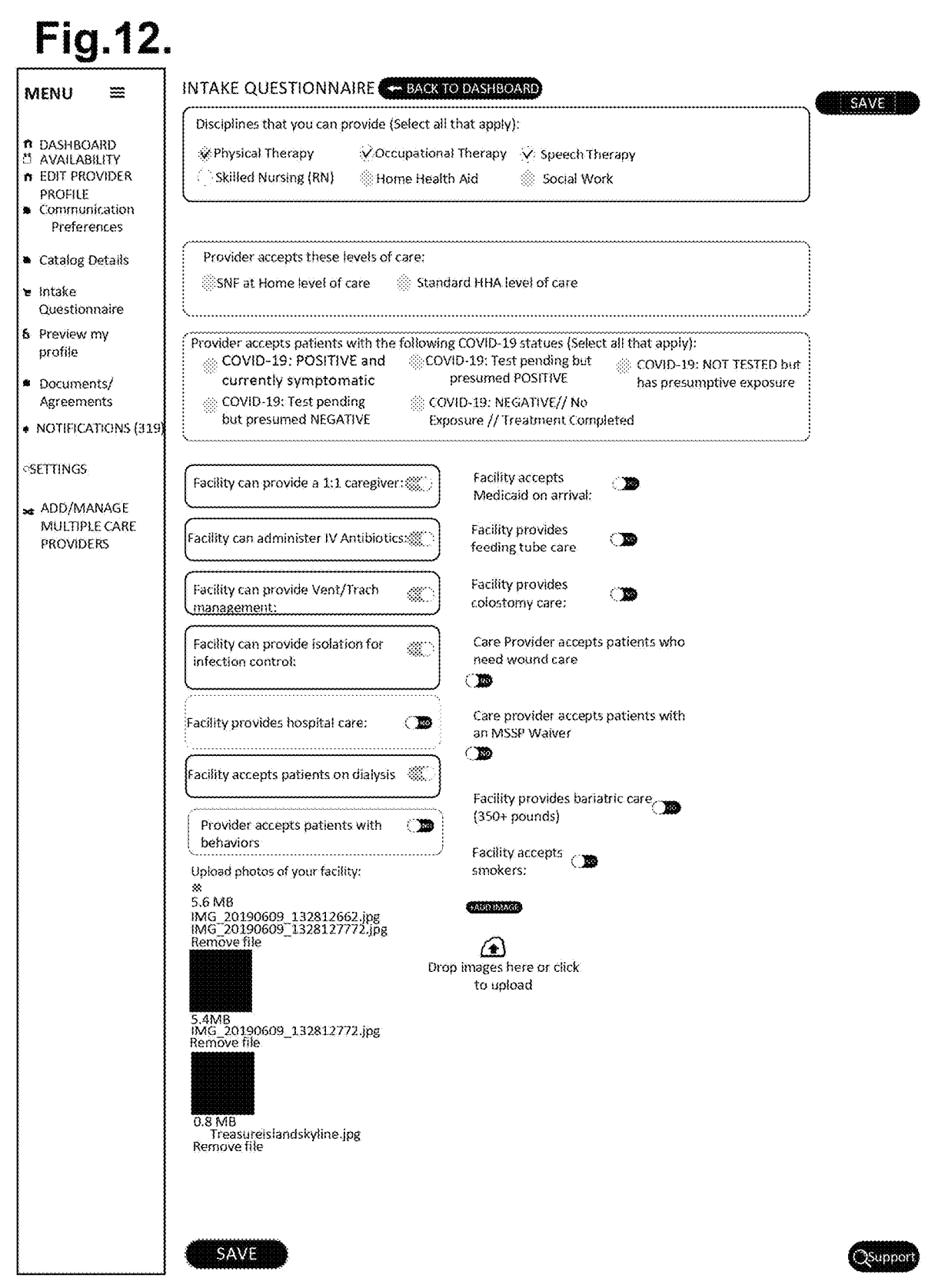

As further described below beginning with the reference to FIG. 2, the data module 29 can use the service provider government data 33 to contact and register with the cloud-computing environment 11 service providers, to remove service providers s that are no longer licensed from consideration for patient discharge, to update availability of beds within LTCFs, and when analyzing a particular service providers for placement of a particular patient, as further described below. The totality of information regarding service providers, obtained both from the government database 32 and other sources, is stored in the relational database as service provider data 30. Additional information that is included in the service provider data can be received from computing devices 164 associated with the service providers, including financial information, medical skills of staff, and pictures or descriptions to be presented to potential users. Such information can be entered via a convenient user interface, such as one shown with reference to FIG. 12. FIG. 12 is a diagram showing an intake questionnaire for service providers in accordance with one embodiment. As further described below with reference to FIG. 5, the availability of beds in an LTCF can be determined by using patient management software tools (not shown) employed by computing devices of an LTCF that are interfaced to the cloud-computing environment 11. The number of the patients being tracked by the tools, with the tools tracking metrics such as progress notes and patient medications, is determined and is used to determine the number of beds being actually used in an LTCF, and correspondingly the number of beds available.

Similarly, data about discharging facilities 37 that have been registered with the cloud-computing environment, such as identifiers of the discharging facilities, contact information for the facilities, and licensing information for the discharging facilities is stored in the relational database 24, and can be added either by the computing devices 13 or by an account manager of the account of the discharging facility associated with the cloud-computing environment 11. The active status of the government license of a discharging facility is verified prior to the registration of a discharging facility with the cloud-computing environment 11, with the registration allowing the discharge facility to input the patient discharge information 21 and trigger the cascade of events that can lead to a patient's discharge.

The government database 31 further stores other data that is necessary to facilitate a discharge. In particular, a discharge of a patient to a service provider generally requires a medical assessment performed by an assessor, a skilled medical professional, such as a registered nurse, to make sure that the patient is fit for a discharge. Conventionally, scheduling such an assessment can take significant time, significantly delaying the discharge of the patient. The background process servers 28 can retrieve from the government database 31 government assessor information 34, such as the assessors' names, medical licensing information such as the license numbers and whether the licenses are current, and contact information. As further described below beginning with reference to FIG. 3, the government assessor information 34 is stored as part of assessor data 35 within the relational database 35 and can be used to identify licensed practitioners capable of performing the medical assessment.

Similarly, the at least one government database 31 can store discharging facility government data 166, which can include identifiers (such as names) and licensing information about a plurality of discharging facilities, such as hospitals (though other kinds of discharging facilities are possible). The government discharging facility data 166 can be used by the background processing servers 28 to verify that a discharging facility that is registered with a database is a licensed facility. The data 166 is stored as part of discharging facility data 37 within the relational database 24.

Each web server 22 further executes a service provider finder 36 that uses the patient discharge information 21, the service data 30, and the assessor data 35 to identify the service providers that are potentially suitable for taking care of the patient. As further described below in detail beginning with reference to FIG. 6, the service provider finder 36 sets matching criteria 162 that includes at least some of the patient discharge information 21, including the desired location of the service providers and a range from that location acceptable for placement (which can be expressed as a radius, though other measures of distance are possible) and the healthcare needs of the patient, including the types of service providers whose care the patient needs. The set of matching criteria 162 further includes the availability of services by the service providers, such as availability of beds in the LTCFs being considered; and the criteria that the service providers must have been previously registered with the cloud-computing environment 11. Other criteria are possible. The matching criteria 162 can be different for each type (or subtype of service providers). For example, if the patient needs an LTCF that can take care of a patient with a broken leg, a pharmacy that can supply medicines that promote bone healing, and a medical equipment provider that can provide custom-made crutches, the matching criteria 162 for LTCF-type service providers will include the requirement for taking care of a patient of the broken leg, the matching criteria 162 for the pharmacy-type care provider will include a requirement for being able to provide the bone-healing-promoting medicines, and the matching criteria 162 for the medical-equipment-type service provider will include a requirement to provide custom-made crutches. As some of the requirements towards one type of service provider are not applicable to other types of providers, making the matching criteria different for each type of the service providers reduces the likelihood that a search for a certain type of a service provider will return no matching result.

The service provider finder 36 executes a search of the service provider data 30 to identify service providers of the desired types that at least partially satisfying the matching criteria: service providers within the desired geographic range that can at least partially match the patient's health-care needs, are available to provide services (such as having beds available at an LTCF), and have been registered with the cloud-computing environment 11. If no matching service providers are identified, the matching criteria 162 are relaxed and the search is repeated one or more times with the modified matching criteria until either matching service providers are found or no more modifications are permitted. For example, initially, the modifying of the matching criteria involves increasing the search range by a predefined amount one or more times as long as the search range remains below a predefined threshold (such as being within the boundaries of the state where the patient is located, though other thresholds are also possible). Once the predefined threshold has been reached, the search range is returned to the original value, but one of the criteria is dropped from the matching criteria set 162 and the search is repeated. In one embodiment, the dropped criteria can be the availability of services (such as beds in an LTCF), though other criteria being dropped first are possible), and an service providers can be found suitable even if the service provider currently is not known to have available beds. If no matching service providers are found with the availability criteria dropped, the range is increased and the search is repeated as described above one or more times until the range increases beyond the predefined threshold. If no matching service providers are found, another criteria is dropped for the set, such as the requirement for the service providers to be registered with the cloud-computing environment 11, and the search range is returned to the original value, and the search is repeated: a service provider that has not previously been registered with the cloud-computing environment, but data about which is obtained from the government database 32. If no matching service providers are found with the availability criteria dropped, the range is increased and the search is repeated as described above one or more times until the range increases beyond the predefined threshold as described above. If no matches are identified, one or more additional criteria may be dropped, with the range is increased and the search is repeated as described above one or more times until the range increases beyond the predefined threshold after each additional criteria are dropped. If after the matching criteria have been relaxed to the greatest permissible extent, the background server 28 performing the matching notifies the computing device 13 through the web server 22 assigned to communicate with the computing device 13 and the elastic balancing service 18 to contact an account manager associated with the system.

Acceptance into the care of one of the service providers may be done by contacting the service providers to confirm that they can accept the patient. However, to further reduce time necessary for the patient discharge into the care, the acceptance of the patient may be automated by the service providers. In particular, the service providers may enable this "auto-accept" feature when registering with the cloud-computing environment 11. When registering with the cloud-computing environment 11 (or at other times), the service provider can use a computing device 164 interfaced to one or more of the Internetworks 12 to interface with the web communication module 168 to establish criteria (such as patient's age, health conditions, lab results, insurance status, and other medical and non-medical information) that can be stored as part of service provider data 30 and that the patient needs to meet in order to "auto-accepted" into the care of the service provider. If the patient meets that criteria (such as if determined by the service provider finder 36), the patient can be accepted into the care of that service provider without direct input from that service provider.

If the service provider has not enabled auto-accept, or if the patient does not meet the auto-accept criteria set up by the service provider, after the matching service providers are identified, the matching service providers for whom auto-acceptance is not performed, are contacted by a contact module 167 implemented by each of the background process servers 28. As further described below with reference to FIG. 8, the contact module 167 contacts each of the identified matching service providers for whom auto-acceptance is not performed with a request to indicate whether these service providers are interested in starting to care for the patient, or, optionally, having the patient, the patient representative, or, optionally, both conduct a tour of the service provider's facility (such an LTCF, which is also indicative of the desire of the LTCF to have that patient placed in that LTCF). The service providers can be contacted via a plurality of communication channels, with the service providers being contacted via different communication channels if they do not respond to the initial communications via a first communication channel. Such communication channels can include a cellular phone 17 of an individual associated with the service provider, a voicemail associated with the cell phone, a fax machine 15 associated with the service provider, and a landline phone 16 associated with the service provider. Other channels are possible. For example, the contact module can send an SMS message to the service providers if the contact information for sending the message is available. Likewise, the communications themselves can be automatically generated voice messages or text messages. The messages are delivered via the Internetworks 12 by External APIs 40 with which the contact module 167 interfaces. A positive or negative response can be received via the same communication channel through which the communication was sent or via a different communication channel. For example, when receiving a call via a cell phone or landline, a service provider employee responding to the call can press a button on the cell phone or the landline phone to indicate a positive or negative response. On the other hand, after receiving a fax, the recipient can call a provided number to respond to the received message. The received responses are presented to the user via the user interface 20, and upon receiving a user selection of one or more of the service providers, the contact module 167 can either contact the selected service provider via one of the External APIs 40 to schedule the tour at a time received from the user, or can provide to the user contact information of the service provider to allow the user to schedule the tour directly.

In a further embodiment, in addition to a simple indication of the willingness to conduct a tour, the responses received from service providers can include a rate at which they would be willing to accept the patient to their care. The s service providers can also be notified by the contact module 167 about rates that one or more other service providers of the same type responded with and be given an opportunity to change their rate one or more time. Thus, the service providers of the same type (such as multiple LTCFs) are allowed to place bids on accepting the patient by communicating their rates to the web servers 22 and modify such rates.

If matching service providers are found and either can auto-accept the patient or have responded affirmatively to request to conduct the tour, information about these service providers is transmitted to the computing device 13 by one of web communication module of one of the web servers 22 via the load balancing service 18 and are presented to the user. A service provider is considered a match if the matching criteria 162 even by 1%: that is an service provider that is within a searched geographic area and that satisfies availability and registration criteria, if they are used, and that is at least a partial match to the medical needs of the patient included in the discharge information 21, is a match that can be presented to the user. In determining the degree of match, some of the patient's healthcare needs can be weighed heavier than others. For example, if the patient is diabetic and is also prescribed therapeutic massage, an LTCF that has staff capable of administering insulin shots but no on-site massage therapist could receive a higher match percentage than an LTCF that has an on-site massage therapist, but no staff capable of administering insulin shots.

The presented information can include the name and location of an service provider, the available services at the services provider (such as a number of beds in that LTCF); languages spoken in that service provider; and how much a particular service provider matches the matching criteria 162 for that provider type, such as percent match. The order in which the matching service providers of the same type are presented can be determined in a variety of ways, including the degree to which the service providers match the matching criteria 162, an alphabetical order, the distance between the service providers and the location included in the discharge information, and a history of the cloud-computing environment's 11 interaction with the service providers. Other ways to sort the results are possible.

Each of the web-servers further executes a discharge module 38, which can take additional steps to facilitate simultaneous or near-simultaneous patient discharge into the care of service providers of different types, thus reducing the time necessary to discharge the patient from the discharging facility. While an assessment 163 of the patient may not be required for discharging the patient into a care of all types of service providers, the assessment 163 may be necessary for other types of providers, such as LTCFs. Such assessment 163 may be performed by staff of the discharging facility, but if not available, the discharge module 38 can take part in making the assessment happen. While a third party (such as the cloud-computing environment 11) may not be always permitted to schedule an assessment of the patient due to limitations of the patient's insurance plan, the discharge module 38 of the web-servers 22 and the contact module 167 of the background process servers 28 can also schedule an assessment of the patient by a skilled medical professional to allow the discharge of the patient to be completed, as further described below beginning with reference to FIG. 2. Whereas conventionally, LTCFs are not contacted until the assessment is performed, the discharge module 38 can schedule the assessment at approximately the same time as the suitable LTCFs (and other types of service providers for which the assessment is necessary) are identified and contacted. As mentioned above, the assessor data 35 includes the temporal availability and the geographic region where the assessors performs the assessment, and the discharge module 38 can identify assessors capable of performing the assessment at the nearest future by comparing the assessor data to the patient location and temporal preferences or restrictions included in the discharge information 21. The discharge module 38 requests the contact module 167 of one of the background process servers, the web communication module 168 of one of the web servers, or both, to contact multiple identified assessors at the same time, sending messages either via the External APIs 40 or via the load balancing service 18 to computing devices 14 of the assessors to indicate whether they will perform the assessment at a specific location during a specific temporal interval. The assessor can send the message from the computing devices 14 to indicate that they will perform the assessment. Upon receiving the indication from one of the assessors, the discharge module 38 will contact the other contacted assessors with additional messages to let them know that their response is no longer needed. The discharge module 38 will also provide the patient discharge information 21 to the assessor who will perform the assessment via a web communication module 168 of one of the web servers.

While or after performing the assessment, the assessor can communicate the results of the assessment to the discharge module 38 by either filling out an assessment form, which can be either a file locally stored on the computing device 14 or be provided through the web-browser 20 or a mobile application executing on the computing device 14, with the form being served by one of the web-servers 22 via the load balancing service 18. The web-browser 20 or the mobile application can also present to the assessor a messaging service, such as a chat box, through which the assessor can send messages to the discharging facility (such as the computing device 13) and receive answers, which may further facilitate the assessment. The received assessments 163 are stored by one of the web-servers 22 in the relational database 24 (or possibly as one of the uploaded files 26 in the file storage 25), and is subsequently provided by the discharge module 38 via the web-communication module of one or more of the web servers 22 to one or more the service that indicated their willingness to have the patient or the representative of the patient tour that LTCF.

Following the optional tour, the user associated with the computing device 13 of the discharging facility notifies the web communication module 168 of the web-server 22 communicating with the computing device 13 if one of the suggested service providers of each of the types is selected. The web-server 22 discharge module 38 arranges the discharge into the care of the selected service providers by notifying the selected service of providers of the selection. The communication module 168 of the web-servers 22 further receive via one of the Internetworks 12 from computing devices 164 associated with the selected service providers a confirmation from the selected service providers that the patient has been discharged to those service providers. The confirmation and the user can be stored in the relational database 24, such as in the discharge information 21 of the patient.

The cloud-computing environment 11 provides an easy way for a system administrator to control the implementation and configuration of the components of the environment. In particular, the cloud-computing environment can present an analytics service interfaced to all components of the cloud-computing environment 11 that can monitor and analyze the activities of the components. In one embodiment, the analytics service 41 be Amazon® Cloudwatch provided by Amazon Web Services, Inc. of Seattle, Washington, though other analytics services are possible. A system administrator use a control console 44 running on computing device 165 connected to a virtual private network 45 (VPN) interfaced to one of the Internetworks 12 can configure the cloud-computing environment 11 and receive the data from the analytics service 41. In a further embodiment, the virtual private network 45 can be omitted.

A system administrator or another developer can also deploy code within the cloud-computing environment 11 from a computing device 46 via a code deployment service 44 and the file storage 25 within the cloud-computing environment 11. In one embodiment, the code deployment service 44 can be AWS CodeDeploy provided by Amazon Web Services, Inc. of Seattle, Washington, though other deployment services are possible. In particular, the code to be deployed is initially passed from the computing device 46 of the developer to a version control repository 48, such a server implementing the Git version control system as well as, or alternatively, BitbucketR servers implanting Jira® software, both provided by Atlassian Pty Ltd proprietary limited company of Sydney, Australia, though other version control repositories are possible. Subsequently, the code is transmitted to a testing service 48, such as Bitbucket® Pipelines service, where the code is tested to identify potential issues. Following the testing, the code is stored within the file storage 25, and the code deployment service 44 is notified that the code has been stored, which triggers the code deployment service 44 to retrieve and deploy the code throughout the cloud-computing environment.

The cloud-computing environment 11 further includes a log service 43, which is interfaced to all other components of the cloud computing environment and which all of the transactions that take place within the cloud-computing environment 11. Thus, the created logs include when particular data from the relational database 24 or the file storage 25, allowing to know when and by whom information about a particular patient was accessed, which promotes security of the patient's information. In one embodiment, the logging service 43 can be DynamoDB provided by Amazon Web Services, Inc. of Seattle, Washington, though other logging services are possible.

The log service 43 and the analytics service 41 are interfaced with at least one backup service 42, which backs up all the data within the cloud-computing environment 11 (being interfaced to them via the connection to the analytics service 41), including the logs created by the logging service 43. In one embodiment, the backup service 42 can be Amazon® Glacier provided by Amazon Web Services, Inc. of Seattle, Washington, though other backup services are also possible. In a further embodiment, the backup service 42 service can interface with a secondary backup service (not shown), which can be located outside of the cloud-computing environment 11, such as Microsoft Azure®, provided by Microsoft Corporation of Redmond, Washington, though other secondary backup services are possible.

As mentioned above, the communications between the load balancing EHR servers 174), 14, 164 are encrypted to preserve the privacy of the exchanged patient data. Similarly, all data being exchanged and stored within the cloud-computing environments 11 is encrypted, including data exchanged between servers 22 and 28, the scheduler 39, and the data stored within and transmitted from the file storage 25 and relational database 24, the backup service 44, the cache 23, and other components. Similarly, communications sent to the External APIs 40 by the background process servers 28 and received from the External APIs 40 by the background servers are similarly encrypted.

The servers 22, 28, 174, as well as computing devices 13, 14, 164, 165, 46 can include components conventionally found in programmable computing devices, such as one or more CPUs, memory, input/output ports, network interfaces, and non-volatile storage, although other components are possible. The servers 22, 28, 174 can each include one or more modules for carrying out the embodiments disclosed herein. The modules can be implemented as a computer program or procedure written as source code in a conventional programming language and that is presented for execution by the central processing unit as object or byte code. Alternatively, the modules could also be implemented in hardware, either as integrated circuitry or burned into read-only memory components, and each of the servers 22, 28 can act as a specialized computer. For instance, when the modules are implemented as hardware, that particular hardware is specialized to perform the communications and analysis that other computers without the hardware cannot be used for that purpose. The various implementations of the source code and object and byte codes can be held on a computer-readable storage medium, such as a floppy disk, hard drive, digital video disk (DVD), random access memory (RAM), read-only memory (ROM) and similar storage mediums. Other types of modules and module functions are possible, as well as other physical hardware components.

Further components, referred to as "services" in the description above, such as services 18, 27, 44, 42, 43 include servers and database necessary for implementing those servers.

Still other components are possible in the system. For example, patients and their caregivers may use personal devices to access data that is provided to the computing devices 13 via the load-balancing service 18.

By coordinating data exchange from a plurality of parties involved in patient discharge in a secure and efficient manner, patient discharge can be significantly accelerated and costs associated with discharge delays significantly reduced. FIG. 2 is a flow diagram showing a method 50 for facilitating multi-provider patient discharge with the aid of a digital computer in accordance with one embodiment. The method 50 can be implemented using the system 10 of FIG. 1, though other implementations are also possible.

Figure 3:
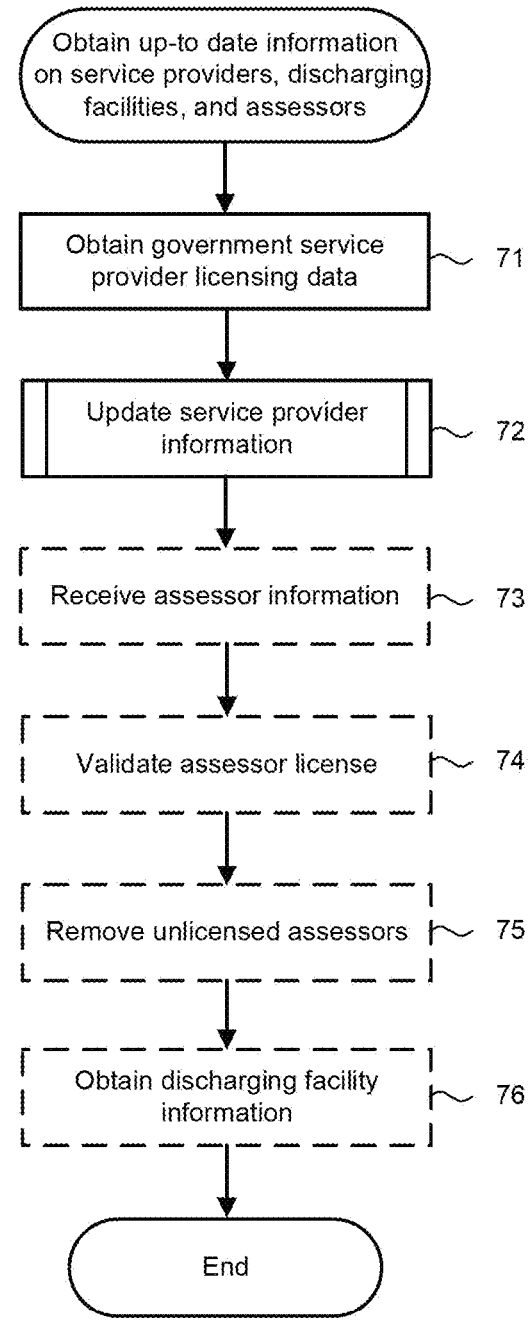
FIG. 3 is a routine for obtaining up-to-date information on service providers, discharging facilities, and assessors for use in the method of FIG. 2 in accordance with one embodiment.

Optionally, if not already present, up-to-date information on service providers, assessors, and discharging facilities is obtained by the background processing servers (step 51), as further described below beginning with reference to FIG. 3. A request for discharging one of the patients is received from by one of the web servers from one of the EHR servers. Patient discharge data is received from a computing device associated with the discharging facility via at least one of the EHR servers and a load balancing service by one of the web servers (step 53), as further described below with reference to FIGS. 10 and 11. Also, as mentioned further below, the discharge information may be received multiple times as updating the information may be necessary.

Whether auto-discharge option is enabled for the discharging facility (step 53) and whether the patient satisfies the auto-discharge criteria (step 54) is checked by one of the web servers, and if the answer is yes for both, the method 50 moves to step 55. If the answer in either step 53 or step 54 is a no, the service provider finder checks whether a discharge confirmation for the patient has been received from an authorized user (such as a social worker or a nurse) associated with the discharging facility has been received (step 56), and if the answer is yes, the method 50 moves to step 55. If no user confirmation of the discharge has been received (step 56), the method 50 ends.

Figure 7:
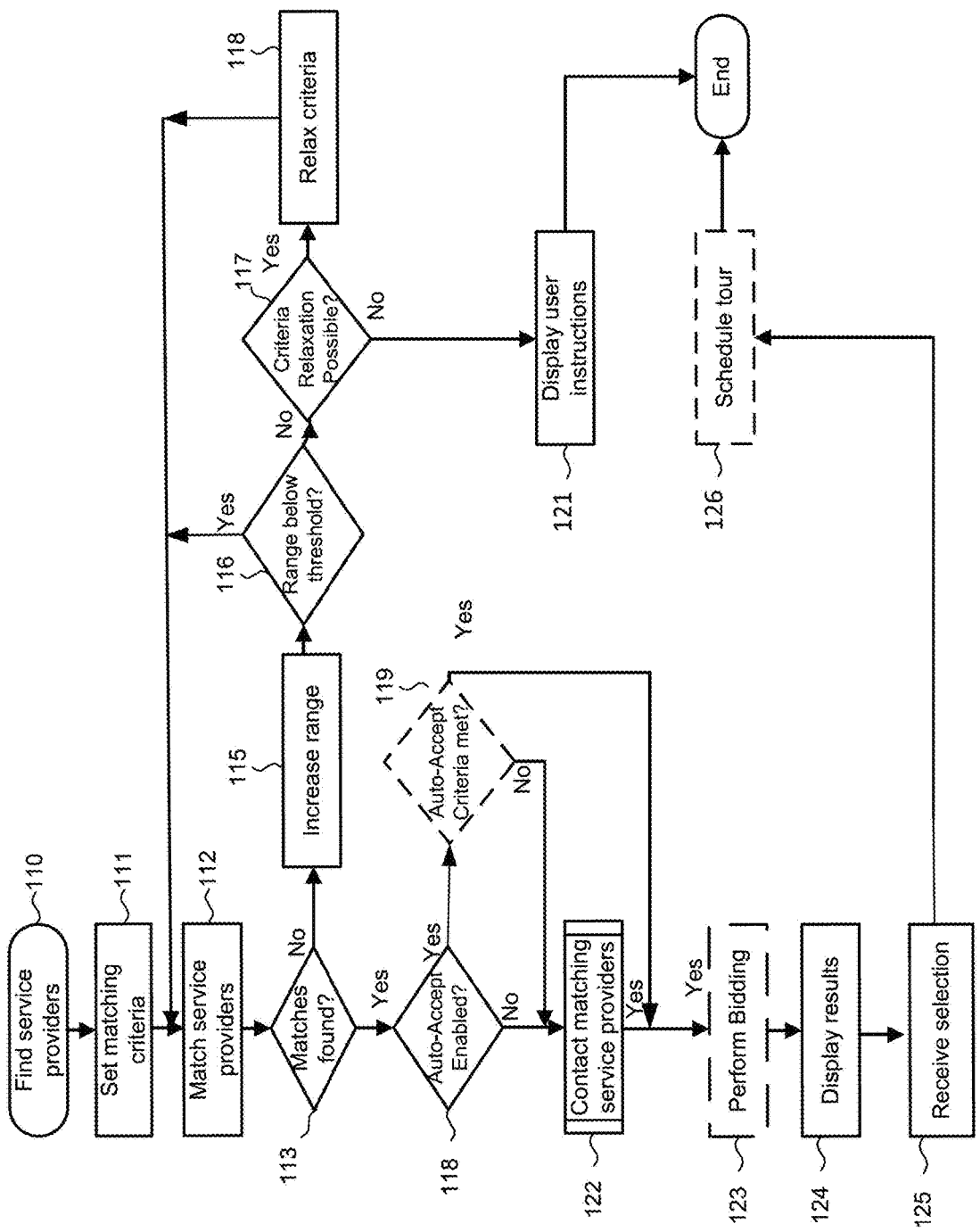
FIG. 7 is a flow diagram showing a routine for finding service providers suitable for the discharge of the patient for use in the FIG. 2 in accordance with one embodiment.

Service providers of each requested types suitable for accepting the patient are identified by the web server and, optionally, tours are scheduled with one or more of the using one of the background processing servers (step 55), as further described below with reference to FIG. 7. At the same time as the scheduling of the tours, one of the web servers optionally (if necessary for any of the types of service providers into whose care the patient is being discharged) determines if an assessment of the patient for the discharge has previously been done and provided to the cloud-computing environment (step 57). If the assessment has been done and the results are accessible to the web server (step 57), the method 50 moves to step 589. If the results of the assessment are not accessible to the web server (step 57), the web server optionally determines if a third party (such as the web server) is allowed to schedule the assessment (step 62), which may not be always possible due to administrative restrictions of the patient's healthcare plan. If the web server cannot schedule the assessment (step 62), the web server optionally sends a message to a computing device (such as via one of the EHR servers) associated with the discharging facility with a request to schedule the assessment (step 63) and the method 50 moves to step 65. If the cloud-computing environment can schedule the assessment (step 62), the web server optionally schedules the assessment using one of the background process servers, as further described below with reference to FIG. 9. The assessment is received by the web server (step 65), either from a computing device associated with the assessing nurse or from a computing device associated with the discharging facility (such as via one of the EHR servers), and the assessment may optionally be made available to service providers selected by the user associated with the discharging facility, such as via logging in by the individual user into a web application maintained by the web communication module of the web servers (step 58).

Discharge into the care of the selected service providers (such as by the discharge module of one of the web servers) is arranged by notifying the service providers regarding the discharge (step 59) and a discharge confirmation is received (such as by the discharge module of one of the web servers) from a computing device associated with the service providers selected for placement (step 60), ending the method 50.

While performance of the patient medical assessment is often required by law in many jurisdictions prior to a discharge of the patient to an LTCF (and possibly other types of medical providers), in a further embodiment of the method 50, the steps relating to the assessment and provision of the assessment to the LTCF can be omitted and a patient discharge can be facilitated without the assessment being performed.

Obtaining up-to-date information on the service providers, assessors, and the discharging facilities allows to determine effective ways to contact these entities and make sure that no unlicensed parties are involved in the discharge of the patient in roles where government licensing is necessary. FIG. 3 is a routine 70 for obtaining up-to-date information on LTCFs, discharging facilities, and assessors for use in the method 50 of FIG. 2 in accordance with one embodiment. Initially, publicly-available government data for service providers (such as an identifier of an LTCF (or another type of service provider), license number, inspection and citation data, status of the license, and expiration date of the license, contact information for the service provider, information about availability of beds (or other types of services), and contact information of the owner of the service provider) and assessors is obtained by one of the background process servers from one or more government servers via an Internetwork (step 71). Obtaining such government data can be done on a recurring basis, such as every day. Obtaining such government data may require comparison of information from multiple sources, such as different spellings of the same provider's name, and reconciling the differences between them as described above with reference to FIG. 1.

Figure 4:
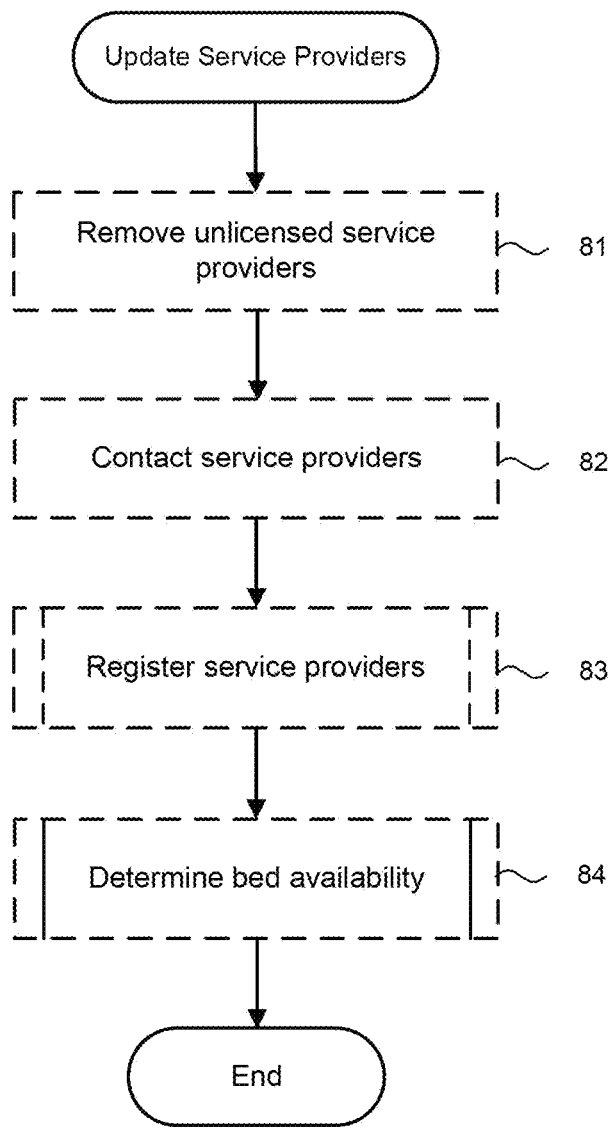
FIG. 4 is a flow diagram showing a routine for updating service provider information for use in the routine of FIG. 3 in accordance with one embodiment.

Service provider data in the relational database is updated based on the obtained government information by one or more of the background process servers (step 72), as further described below with reference to FIG. 4.

Optionally, information of assessors wishing to register with the cloud-computing environment, such as the assessors name, license number, and contact information is received by the cloud-computing environment (such as by one of the web servers), such as from computing devices associated with such assessors, though other sources are also possible, and stored in the relational database and possibly in the file storage (step 73). The licenses of all of the assessors whose information is stored in the relational database is validated using the information retrieved from the government servers by one or more of the background process servers (step 74), and any assessors whom the data obtained from the government servers does not show having a valid license are removed by one or more of the background process servers from the list of assessors who could be contacted to schedule a patient assessment (step 75). Finally, optionally, information about discharging facilities is received from these discharging facilities, such as by one of the web servers via the load balancing service, and from the government database, and if the discharging facility is shown to have an up-to-date government license (as verified by the information retrieved from the government database, the discharging facility is registered with the cloud-computing environment (allowing the discharging facility to provide patient discharge information and receive the matching service providers) and the information about the discharging facility is stored in the relational database (step 76), ending the routine 70. The information about the discharging facilities can be received by the cloud-computing environment from the computing devices associated with these discharging facilities, such as via the load balancing service, or be provided to a system user (such as an account manager) and input into the cloud-computing environment.

Using up-to-date service provider information allows to avoid contacting service providers who are no longer licensed for their services. FIG. 4 is a flow diagram showing a routine 80 for updating service provider information for use in the routine 70 of FIG. 3 in accordance with one embodiment. The routine 70 can be performed by one or more of the background process servers, with web servers being employed as described below. Optionally, if a comparison of the government information to information within the relational database shows any of the service providers as no longer licensed, the service providers are removed from a list of the service providers considered for possible discharge of the patient (step 81). Optionally, service providers whose information has been received from the government server are contacted, either by the web servers or the background processing server depending on the way of communication employed, with an invitation to register with the cloud-computing environment (step 82). Optionally, if one or more of the contacted service providers respond to the invitation, the service providers are added by one or more background process servers or web servers to the list of registered service providers within the relational database (step 83), as further described with reference to FIG. 6. Bed availability of one or more LTCFs registered with the cloud-computing environment is subsequently determined (step 84), as further described below with reference to FIG. 5, ending the routine 80.

Figure 5:
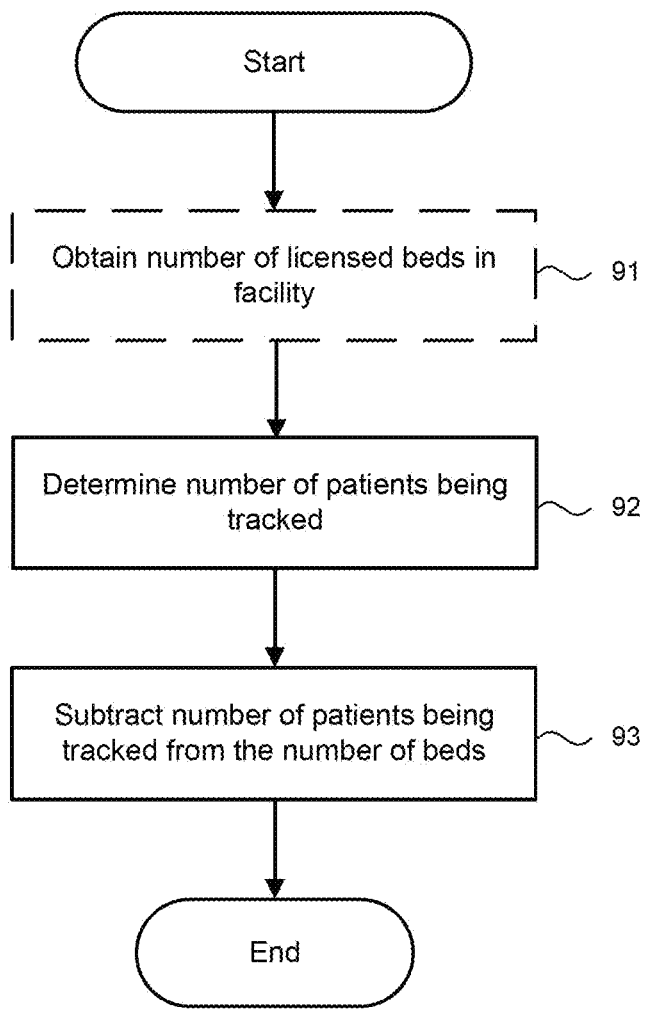
FIG. 5 is a flow diagram showing a routine for determining availability of beds in an LTCF for use in the routine of FIG. 4 in accordance with one embodiment.

While the registered LTCFs periodically update the number of licensed beds available in those LTCFs with the cloud-computing environment, such information may be out-of-date and not useful in finding matching LTCFs when the availability of beds is one of the criteria used. As described above, computing devices used by LTCFs can use patient management tools software interfaced to the web servers via one of the Internetworks, which can be used to track a variety of patient-related metrics, such as progress notes, and the medications that a particular patient is taking (though other metrics are possible), and report the tracked data to the cloud-computing environment; the number of patients being tracked can be used to determine the availability of beds in an LTCF. FIG. 5 is a flow diagram showing a routine 90 for determining availability of beds in an LTCF for use in the routine 80 of FIG. 4 in accordance with one embodiment. Initially, optionally, if not already available, a number of beds an LTCF that has been provided during the LTCF registration is retrieved by one of the background process servers (step 91). The number of patients for whom the tracking software is used is determined by the background process server (step 92). The number of available beds is determined by the background process server by subtracting the number of patients for whom medications are being tracked from the total number of beds in that LTCF (step 93), ending the routine.

Figure 6:
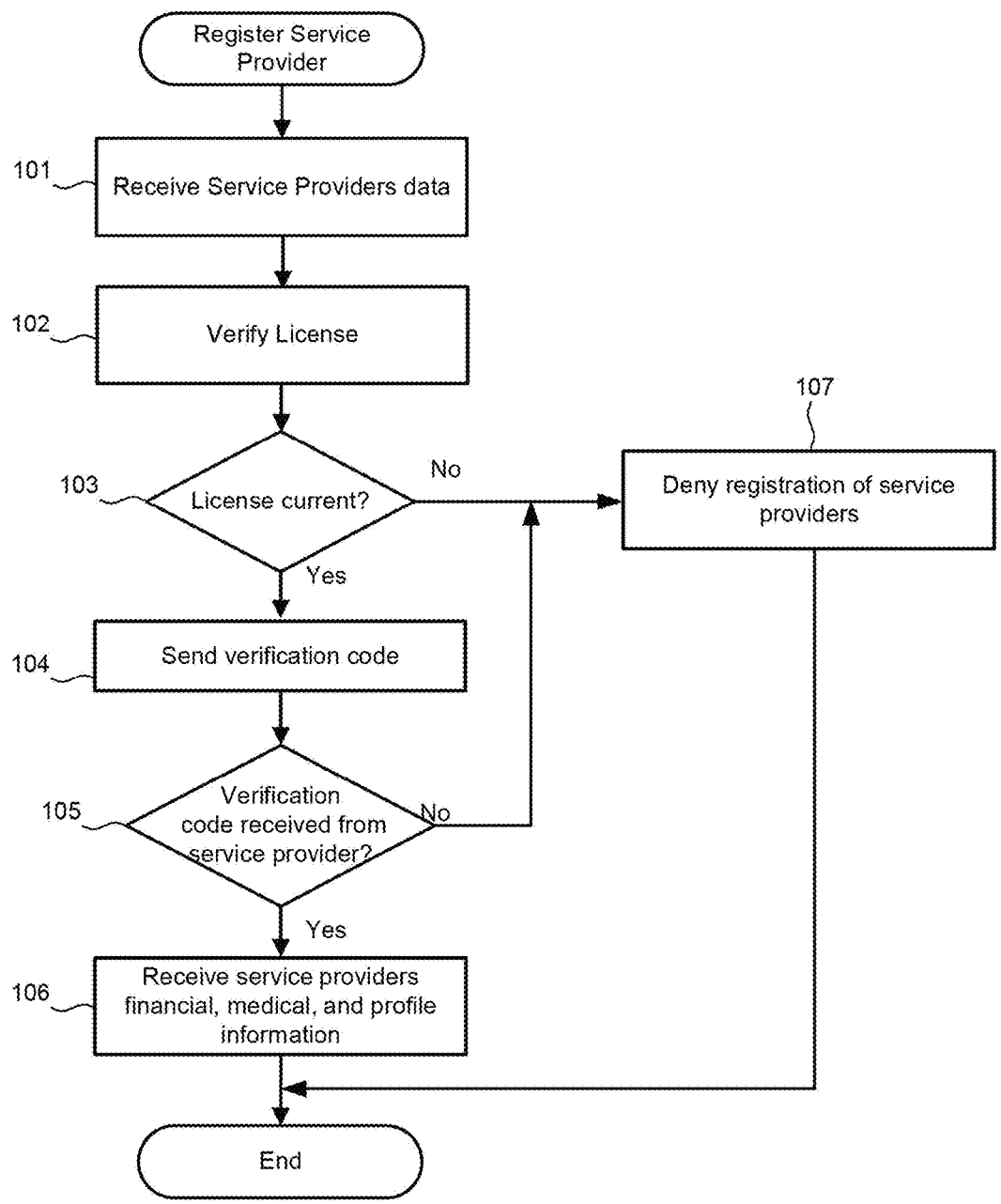
FIG. 6 is a flow diagram showing a routine for registering a service provider with the cloud-computing environment in accordance with one embodiment.

Registering a service provider with the cloud-computing environment requires to verify that communications purportedly being received from that service provider are genuine. FIG. 6 is a flow diagram showing a routine 100 for registering a service provider with the cloud-computing environment in accordance with one embodiment. Initially, registration data is received from an service provider that includes the name of the owner of the service provider, an identifier (such as a name) of the service provider, licensing information of the service provider, and contact information of the service provider by one of the web servers (step 101). The registration data can further include whether the auto-accept option is enabled for the service provider and what criteria that the patient must meet in order to be accepted into the care of that service provider. Whether the license of the service provider (if a license is necessary for that type of service provider) is current is determined by the web server using the licensing information obtained from the government server (and maintained in the relational database) (step 102), and if the service provider's license is not determined verified (step 103), the service provider is denied registration and is removed from the list of service providers that are considered for a patient being discharged into (step 107), ending the routine 100. If the license has been verified as current (step 103), a verification code is sent by one of the background servers via one of the External APIs to contact information of the service providers that is present in the data retrieved from the government database (step 104). In one embodiment, the verification code is sent by one of the background process servers via one or more of the External APIs to at least one of a landline phone number and a fax number associated with the service provider, though in a further embodiment, other communication channels can be used. If an individual associated with the service provider transmits the verification code back to the cloud-computing environment (105), either via the same or different communication channel than the one used to transmit the verification code, the information being received for the registration of the service providers is determined to be genuinely coming from the service provider, and the registration is completed by receiving from the service provider additional data, such as financial and billing information of that service provider, additional medical information associated with the service provider, and allowing the service provider to provide profile information, such as a textual description and an image that can be displayed to a user associated with discharging facility when information about the service provider is presented (step 106), ending the routine 100. If no verification code is received within a predefined amount of time, then the registration is denied (step 107), ending the routine 100, as the user with whom the cloud-computing environment was initially interacting lacks access to the communication devices whose contact information is provided to the government and is thus likely not associated with the service provider.

Taking into account multiple matching criteria allows to find service provider most suited for placement of the patient. Further, by having a separate set of matching criteria for each type of service provider, probability of receiving no matches for one particular type is reduced. FIG. 7 is a flow diagram showing a routine 110 for finding service providers of multiple types suitable for the discharge of the patient for use in the FIG. 2 in accordance with one embodiment. The routine 110 is run separately (though at the same time) for each type of service providers to whose care the patient needs to be discharged, and thus the execution of the routine 110 can run differently for different types of service providers. Initially, a set of matching criteria is obtained by one of the web servers for each type of the service providers into whose care the patient must be discharged based on the discharge information for the patient (step 111). The matching criteria can include a requirement for availability of beds within an LTCF (or other kinds of service availability for other types of service providers), a requirement that a service provider is registered with the cloud-computing environment, the medical care needs of the patient that need to be met by the service provider of that type, the desired geographic location of a service provider and a permissible distance range from the desired location. Other criteria are possible.

The service providers are matched to the matching criteria by the web server by comparing the data associated with the service providers of a particular type, such as location, registration availability of beds, and medical care capabilities to the matching criteria for that service provider type, to identify service providers of each type that at least partially match patient discharge needs (step 112). If no matches are found (step 113), the range is increased by the web server by a predefined amount (step 115). Whether the range is below the threshold (such as the area covered by that range being without the geographic boundaries of the patient is located) is determined by the web server, and if the range is below the threshold (step 116), the routine 110 returns to step 112 and another match is performed. If the range exceeds the threshold (step 116), whether the matching criteria used for that type of service providers can be relaxed is determined by the web server (step 117). Such relaxation can include removing one of the criteria from the set, such as the requirement for an LTCF to have available beds or for the service provider to be registered with the cloud-computing environment. If the criteria relaxation is possible (step 117), the matching criteria is relaxed (step 118), and the routine 110 returns to step 112, where the matching is repeated using the relaxed matching criteria set. If the criteria relaxation is not possible (such as if only a single criterion is left in the set) (step 117), the user associated with the discharging facility who provided the discharge information is sent a message by the web server to contact his or her account representative as no suitable matches for that particular service provider type could be found (step 121). In a further embodiment, additional steps can be performed by the web servers 121 to attempt to contact and register additional service providers if no further relaxation of the matching criteria in step 117 is possible without sending the message to contact the account manager.

As further described above with reference to FIG. 1, if there are some matching service providers, even partial matches, that are identified by the web server step 113), the web server checks if the auto-accept feature is enabled for those matches (step 119) and if yes, whether the patient meets the auto-accept criteria for those matches (step 112). If the auto-accept criteria are met, the routine 110 moves to step 123. If the auto-accept feature for at least some of the matches is not enabled (step 119) or the auto-accept criteria are not met for at least some of the matching service providers (step 120), those service providers for whom auto-acceptance of the patient is not possible are contacted by one or more of the background servers via the External APIs to indicate whether they would be willing to accept the patient into the care, and if applicable for that type of provider, have the patient or the representative of the patient tour that service provider (step 122), as further described below with reference to FIG. 8. Optionally, in addition to the providing an answer to whether they are interested to have the patient tour the facility (or other indication of interest to accept the patient), the contacted service providers (and service providers who can auto-accept the patient) can indicate a rate at which they would be willing to accept the patient to into their care; the service providers can also be notified via, for example, the same communication channel through which they provided the bid by one of the background process servers or one of the web servers, the rate quoted by other service providers of the same type and allowed to modify their rate, thus effectively allowing the service providers to bid for the placement of the patient (step 123). Following the expiration of a predefined period of time, information about those matching service providers for whom auto-acceptance of the patient is possible or that have responded that they are willing to accept the patient (or at least have the patient or the representative tour that service provider) is displayed to a user associated with the discharging facility (step 124). The displayed information can include the degree to which the service provider match the matching criteria, the location of the service provider, the number and kind of beds in an LTCF (or other indications of service availabilities for other types of service providers), and the medical care capabilities of those service providers, though other displayed information is possible. The order in which the service providers are displayed can be based on a variety of factors, including the degree to which the service providers match the matching criteria, the daily rate of those service providers, and previous interactions with those service providers. Other ways to sort the information about the service providers are possible.

A user selection of one or more of the displayed service providers of each of the requested types for which suitable matches were found is received (step 125) and optionally arrangements for scheduling a tour of the selected service provider are made (step 126), ending the routine 120. In a further embodiment, the optional tour is arranged before a selection of the service providers is made. In one embodiment, the cloud-computing environment can provide the user associated with the discharging facility the contact information of a selected service provider to allow the user to schedule the tour. In a further embodiment, the cloud-computing environment can directly contact the selected service provider and schedule a tour at a time received from the user that is also acceptable to the service provider.

Figure 8:
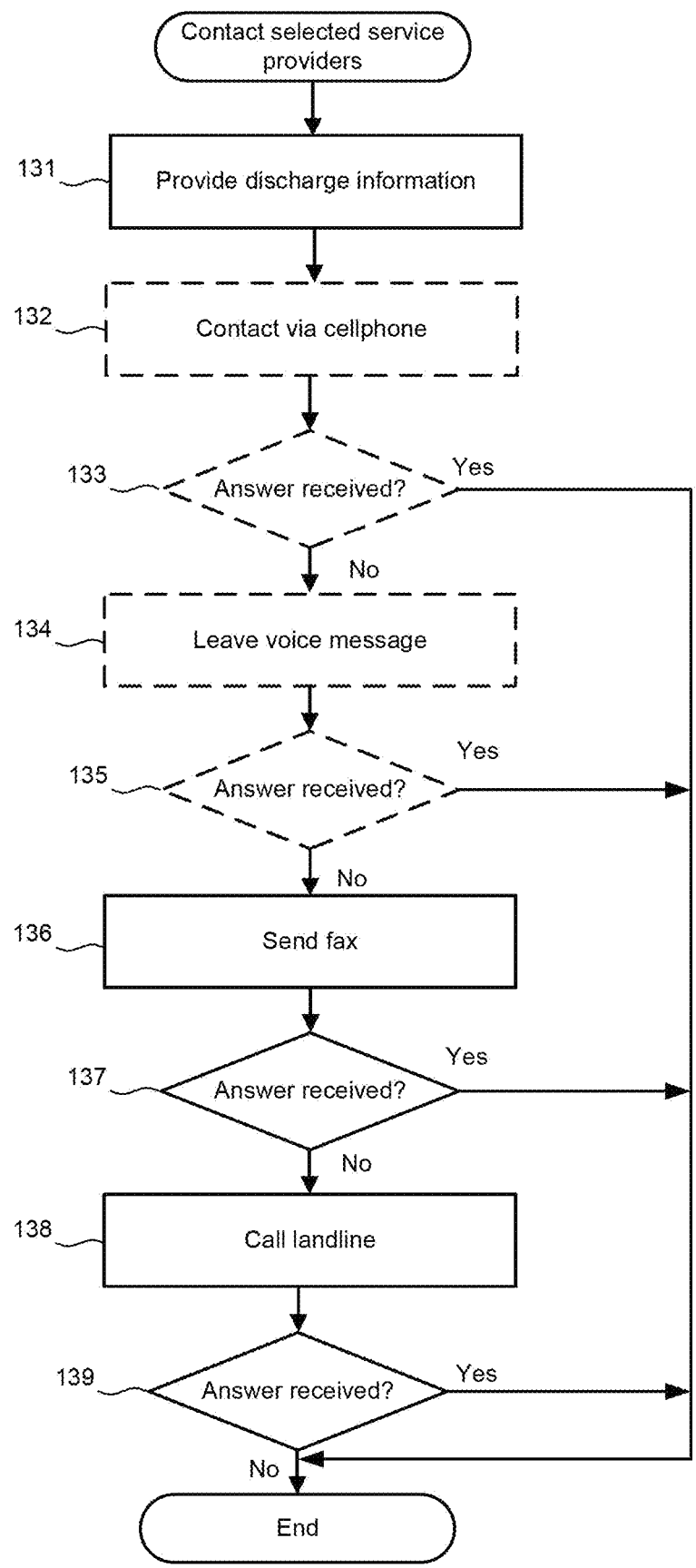
FIG. 8 is a flow diagram showing a routine for contacting matching service providers for use in the routine of FIG. 7 in accordance with one embodiment.

The background process servers can contact matching service provider in a variety of ways to maximize the chance of receiving the response. FIG. 8 is a flow diagram showing a routine 130 for contacting matching service provider for use in the routine 120 of FIG. 7 in accordance with one embodiment. While the description below references contacting one of the service providers, multiple service providers can be contacted in the same way simultaneously by the background process servers via the External APIs. Initially, at least a portion of the discharge information regarding the patient is provided via to all of the matching service providers, such as via being available on a webpage that the users associated with an service provider can access via one of the Internetworks, the load balancing service, and the web servers; other ways of providing the information are possible, such as sending e-mails or faxes to addresses associated with the service providers by the background servers via one or more of the External APIs (step 131). Optionally, if a cellular phone number of a service provider is available, one or more of the background process servers contacts via the External APIs a cellular phone associated with each of the service providers with a voice message (generated by the background process or the External APIs) to check the discharge information about the patient and to indicate whether the service provider is willing to have the patient or the patient representative tour that service provider (or in a further embodiment, to otherwise indicate interest in accept the patient) (step 132). If a representative of the service provider who answers the call provides a positive or a negative answer (such as by pressing a button on the cell phone, with the instructions to do so being included in the message) (step 133), the routine 130 ends. If no answer is received (step 133), optionally, depending on whether the initial call was placed, the generated voice-message is left at the voicemail box associated with the cell phone (step 134). If the service providers provides an answer to one of the background servers or one of the web servers via one of the Internetworks within a predefined amount following the leaving of the voice message (step 135), the routine 130 ends. If no answer is received within a predefined amount of time (step 135), or if the steps 131-134 were not performed, the background process server sends via one of the External APIs a fax to a fax number associated with the service provider, with the fax including the same content as described above with reference to the voice message (step 136). If a response from the service provider is received during a predefined amount of time following the sending of the fax (step 137), the routine 130 ends. If the response is not received within a predefined amount of time (137), the background process server sends the voice message via one of the External APIs to a landline phone associated with the service provider (step 138). The routine 130 regardless of whether the answer is received within a predefined period of time following the initiation of the call to the landline (step 139).

Figure 9:
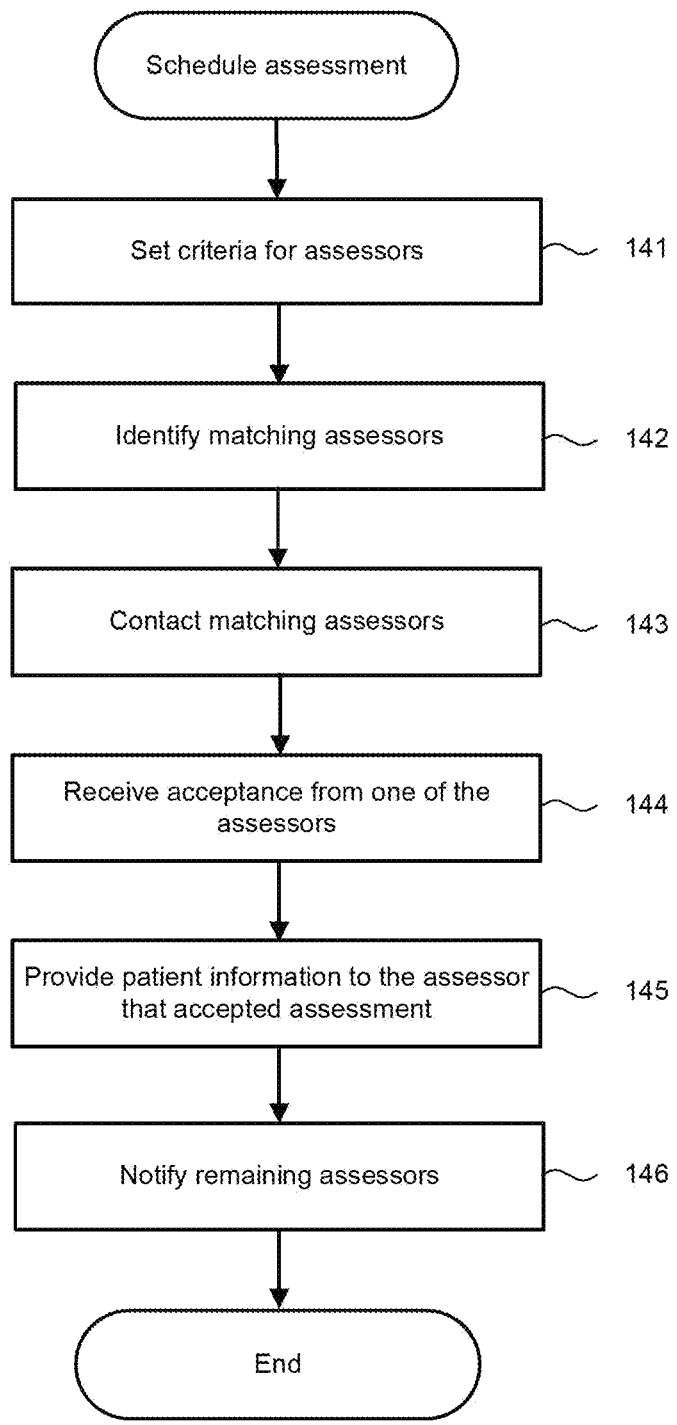
FIG. 9 is a flow diagram showing a routine for scheduling an assessment of the patient for use in the method of FIG. 2 in accordance with one embodiment.

Arranging an assessment of the patient while also identifying the LTCFs (and other types of service providers) where the patient can be discharged allows to accelerate the discharge of the patient. FIG. 9 is a flow diagram showing a routine 140 for scheduling an assessment of the patient for use in the method of FIG. 2 in accordance with one embodiment. A set of criteria for selecting the assessors is set by one of the web servers based on the received patient discharge information (step 141). The criteria includes the geographic location of the patient who needs to be assessed and the desired time for the assessment to be performed (which can be obtained from the patient's discharge information). One or more assessors whose geographic availability for performing assessments and temporal availability, as recorded in the assessor data in the relational database, matches the assessor selection criteria are identified by one of the web server (step 142). The matching assessors are contacted by one or more of the background processing servers, either through one or more web-servers or through the External APIs, with a message to provide a response via their computing devices whether that assessor will perform the patient assessment at a specified time and location (step 143). The response that one of the assessors will perform the assessment is received from that assessor by the background process server or the web server (step 144), and the discharge information regarding the patient is provided to the assessor that responded by one or more of the background servers via the External APIs or by the web server, such as via being available on a webpage that the assessor can access by logging in via one of the Internetworks, the load balancing service, and a web servers; other ways of providing the information are possible, such as by e-mailing the discharge information to the assessor, though still other ways to provide the information are possible (step 145). The remaining assessors are notified by the background process server or the web server that their response is no longer needed as the assessment has been scheduled (step 146), ending the routine 140.

Figure 10:
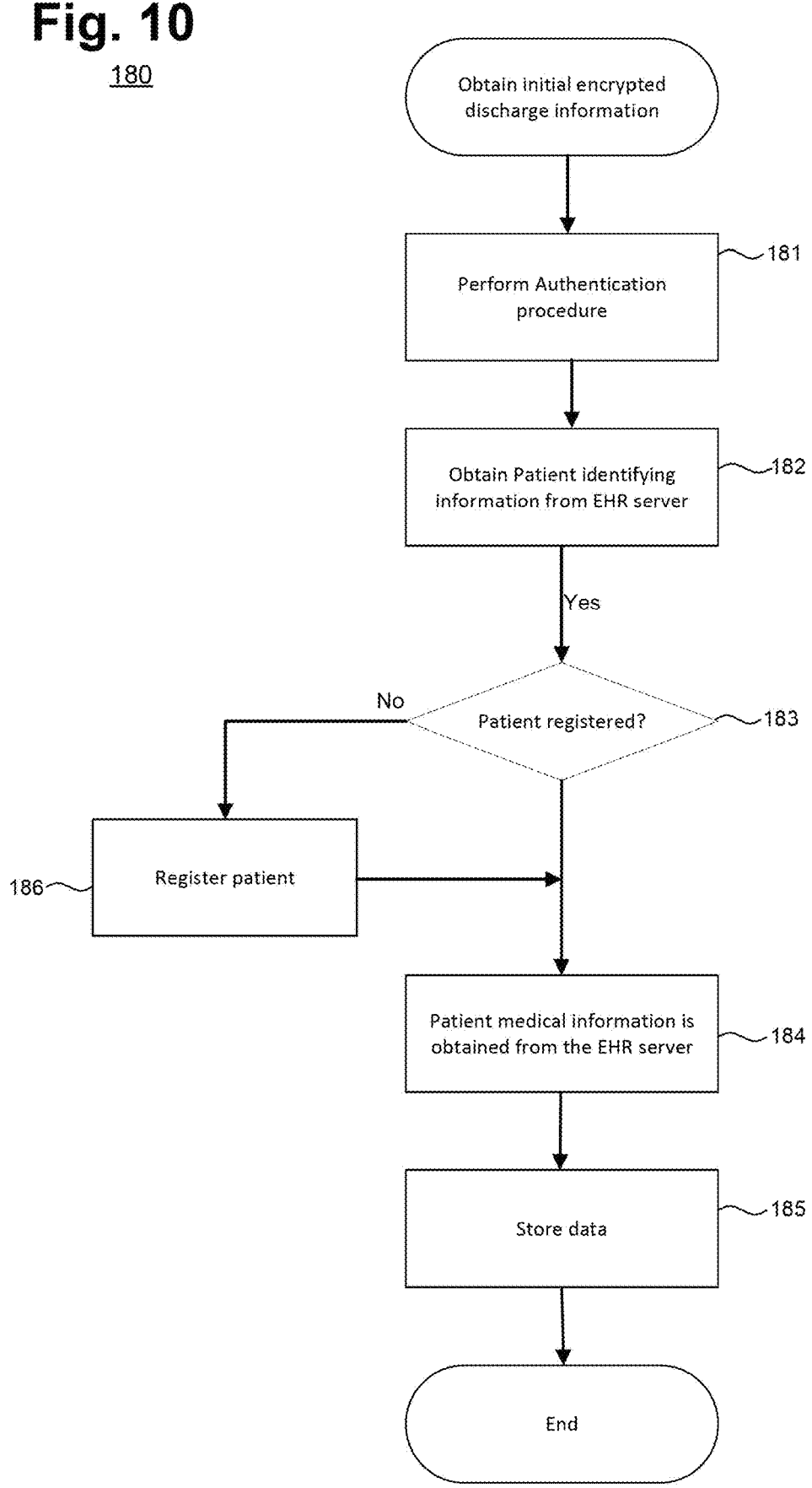
FIG. 10 is a flow diagram showing a routine for initially obtaining patient discharge information for use in the method of FIG. 2 in accordance with one embodiment.

Having the patient discharge information is essential for finding suitable service providers for the patient. The patient discharge information can be obtained initially, at the initiation of the discharge, and can also be updated as necessary. FIG. 10 is a flow diagram showing a routine 180 for initially obtaining patient discharge information for use in the method 50 of FIG. 2 in accordance with one embodiment. An authentication procedure between one of the web servers and one of the EHR servers is performed as described above with reference to FIG. 1 (step 181). Upon passing the authentication (step 181), the web server receives patient identifying information from the EHR server, such as patient name, social security, and birth date (though other identification information is possible) (step 182). The web server uses the patient identification information to check if the patient has already been registered with the cloud computing environment (step 183), and if the patient has been registered (step 183), requests and receives from the EHR server remaining patient discharge information, including the patient's medical information (step 184), which is stored in the encrypted relational database 24 and the encrypted file storage as described above (step 185), ending the routine 180. If the patient is not registered with the cloud computing environment (step 183), the web server registers the patient by storing the patient identifying information within the encrypted relational database (step 186), and the routine 180 moves to step 184.

Figure 11:
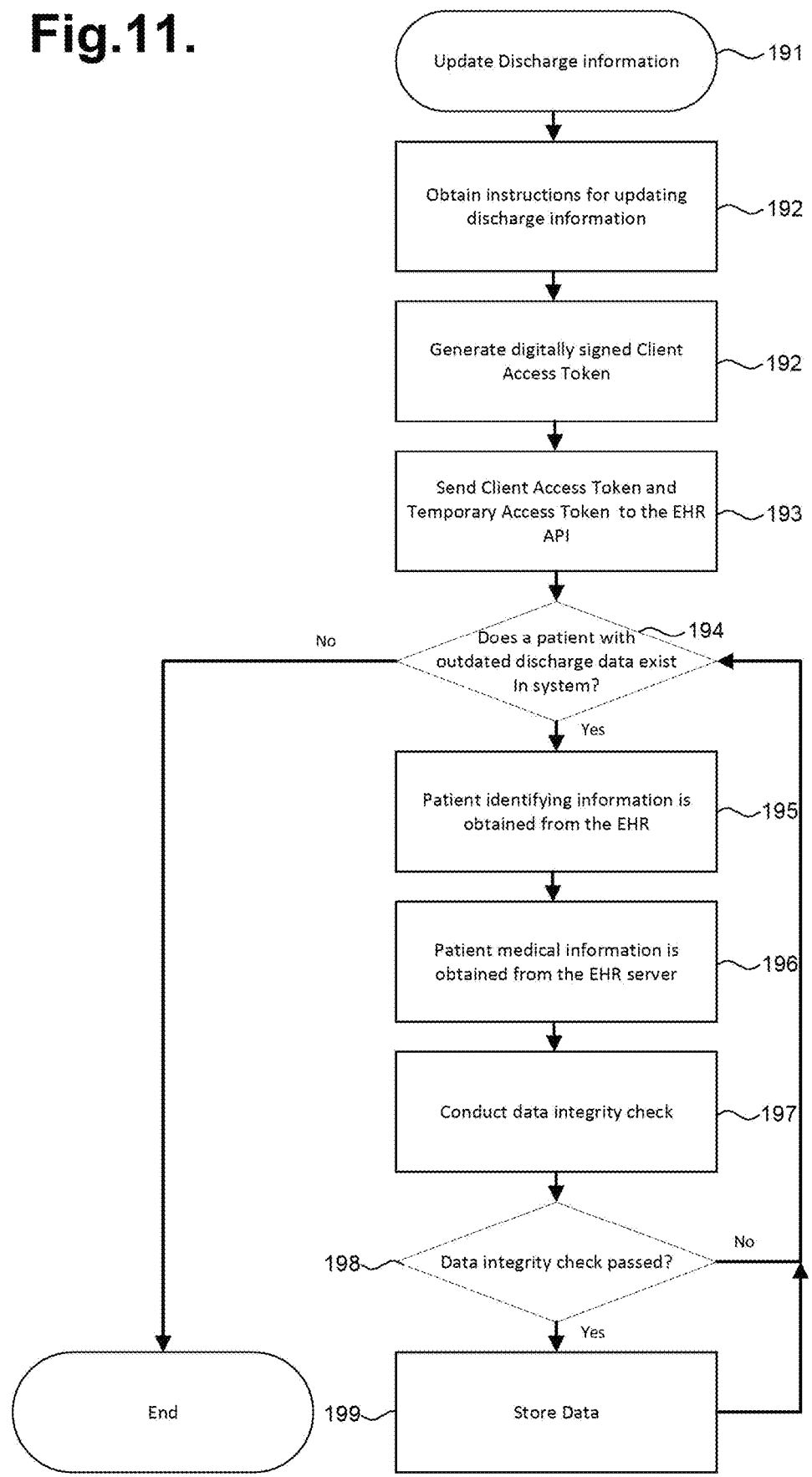
FIG. 11 is a flow diagram showing a routine for updating patient discharge information for use in the method of FIG. 2 in accordance with one embodiment.

Regularly updating the patient discharge information allows to place the patient into the care of service providers whose care remains a good fit for the patient. FIG. 11 is a flow diagram showing a routine 110 for updating patient discharge information for use in the method 50 of FIG. 2 in accordance with one embodiment. Instructions from the service providers regarding when the discharge information needs to be updated are received by one of the web servers (step 191). Authentication between one of the background servers (communicating with the EHR server through a web server) performing the update and an EHR server is performed, such as by the background server generating a digitally signed client access token (192) and the client access token and a temporary access token (previously received from an EHR server) are sent by the worker to the EHR Server (193), though other ways to perform the authentication are possible. One or more of the background servers checks whether there is any patient whose discharge information in the cloud-computing environment has not been updated in accordance with instructions provided by a service provider selected for accepting the patient into that provider's care (step 194). If no such patient exists (step 194), the routine 190 ends. If a patient like that exists (step 194), a worker is assigned to first obtain the patient's identifying information step (195) and then the remaining discharge information, including the patient's medical information (step 196). A data integrity check is performed on the obtained patient information, such as by checking that the obtained discharge information is consistent with previously obtained patient discharge information (step 197). If the integrity check is passed (198), the obtained updated discharged information is stored in the encrypted relational database and the encrypted file storage as described above (199), and the routine moves to the next patient for whom the data needs to be updated. If the integrity check is failed (such as if for a patient who is previously described as an amputee in the earlier discharge data, the updated medical data includes mention of all four limbs) (step 198), the routine moves to the next patient. Once the data for all of the patients is updated (or fails to update due to a failure of the integrity check for one or more of the patients) (step 194), the routine 190 ends.

While in the description above, the discharging facility is referred to as a hospital, in a further embodiment, the patient could use the system and method described above to personally select a LTCF and be "discharged" into that LTCF from the patient's home, with the computing device 13 being associated with the patient or the patient's non-hospital representative. Further, the discharging facility referenced in the system and method above can be any state licensed medical facility, including an LTCF looking to discharge a patient to another LTCF.

While the invention has been particularly shown and described as referenced to the embodiments thereof, those skilled in the art will understand that the foregoing and other changes in form and detail may be made therein without departing from the spirit and scope of the invention.

What is claimed is:

1. A method for cloud-based facilitation of multi-provider patient discharge with the aid of a digital computer, comprising:

obtaining, by one or more of a plurality of background process servers comprised within a cloud-computing environment, information regarding a plurality of service providers of different types located in multiple jurisdictions, the service provider information comprising a geographic location of each of the service providers within one of the multiple jurisdictions and care capabilities of the service providers;

receiving, via one of a plurality of Internetworks, by a load balancing service comprised within the cloud-computing environment and implemented by one or more servers, from a computing device associated with one of a plurality of discharging facilities, each discharging facility located in one of the multiple jurisdictions, encrypted discharge information for one of a plurality of patients, each patient located in one of the multiple jurisdictions, the discharge information comprising care needs of the patient, medical information of the patient, and geographic preferences of the patient for being discharged to a care of the service providers of at least two of the types;

providing, by the load balancing service, the received discharge information to one of a plurality of web servers comprised within the cloud computing environment, and assigning, by the load balancing service, to perform encrypted communication with that computing device to that web server, wherein the web servers and the background process servers communicate via a message queuing service comprised within the cloud computing environment, and wherein the web server stores session data regarding the encrypted communication;

updating by the cloud-computing environment the received discharge information comprising retrieving the updated discharge information via a WebSocket API based on only a single user command and providing via a user interface a bar showing a progress of the retrieval;

comparing, by the web server, the service provider information to the updated discharge information for the patient;

identifying, by the web server, one or more of the service providers of each of the at least two types suitable for the patient based on the comparison;

identifying, by the web server, at least one suitable service provider of each of the at least two types willing to accept the patient to their care;

causing at least in part the patient to be discharged to the care of one of the willing service providers of each of the at least two types by one or more of the web servers; and receiving by one or more of the web servers from computing devices associated with the willing service providers to whose care the patient has been discharged confirmations that the patient has been discharged to the care of those service providers.

2. A method according to claim 1, comprising:

encrypting the medical information of the patient as at least one encrypted file; and storing the at least one encrypted file in an encrypted file storage.

3. A method according to claim 2, wherein the discharge information further comprises identifying information of the patient, further comprising:

encrypting the identifying information of the patient; and storing the encrypted identifying information of the patient in an encrypted database different than the encrypted file storage.

4. A method according to claim 1, comprising:

separating the discharge information into a plurality of data items; and presenting a plurality of the data items separately via a user interface.

5. A method according to claim 1, further comprising:

obtaining from one of the service providers instructions for updating the discharge information, wherein the updating the is performed in accordance with the instructions; and providing the updated discharge information to the one service provider.

6. A method according to claim 5, wherein the instructions comprise one of a schedule for updating the discharge information and a command to update the discharge information upon receipt of the command.

7. A method according to claim 5, further comprising:

performing an integrity check upon the updated discharge information; and upon the updated discharge information failing the integrity check, providing the one service provider a message that the update of the discharge information has failed.

8. A method according to claim 5, further comprising:
scheduling performance of the updating of the discharge information in a queue, wherein updates of discharge information associated with a plurality of remaining ones of the patients are also scheduled in the queue;
assigning at least one worker executed by one of the background servers to perform each of the updates in the queue, wherein the workers perform the updates in parallel.

9. A method according to claim 5, wherein care capabilities of the service providers comprises subspecialties of the service providers.

10. A method according to claim 1, further comprising:
obtaining the information regarding the service providers by parsing one or more websites.

11. A method according to claim 10, wherein the information regarding one of the service providers is parsed from multiple ones of the websites.

12. A method according to claim 11, wherein identification information of the one service provider differs on one of the websites from another one of the websites, further comprising:
comparing the identification information of the one service provider on the websites;
identifying differences between the identification information based on the comparison;
assigning weight to the identified differences; and
identifying a match between the identification information based on the weighed differences.

13. A method according to claim 1, further comprising:
setting criteria for automatic patient discharge from the one discharging facility;
comparing at least a portion of the discharge information of the patient to the automatic patient discharging criteria,
wherein the load balancer is provided the encrypted discharge information based on the comparison.

14. A method according to claim 1, further comprising:
sending, by one or more of the background process servers, to one or more computing devices associated with each of the identified service providers, using one or more external APIs, via one or more of the Internetworks, one or more requests to indicate an interest of that service provider in providing services to the patient; and
receiving, by one or more of the background process servers, via one or more of the Internetworks, a response to the request from at least one of the service providers; and
marking the responding service provider as willing to accept the patient based on the response.

15. A method according to claim 14, further comprising:
receiving, by the web server, via one or more of the Internetworks, from the computing device associated with the discharging facility, a selection of one of the service providers of each of the at least two types that provided the response.

16. A method according to claim 1, further comprising:
receiving criteria for automatic patient acceptance to the care of one or more of the service providers;
comparing the updated discharge information for the patient to the automatic patient acceptance criteria; and
marking one or more of the service providers as willing to accept the patient based on the comparison.

17. A method according to claim 1, wherein the service providers comprise one or more of a long term care facility, a post-acute care facility, a pharmacy, and a medical equipment provider.

* * * * *